(12) United States Patent
Kato

(10) Patent No.: US 11,419,501 B2
(45) Date of Patent: Aug. 23, 2022

(54) FLUORESCENCE OBSERVATION DEVICE AND FLUORESCENCE OBSERVATION ENDOSCOPE DEVICE

(71) Applicant: OLYMPUS CORPORATION, Hachioji (JP)

(72) Inventor: Shuichi Kato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 878 days.

(21) Appl. No.: 16/229,435

(22) Filed: Dec. 21, 2018

(65) Prior Publication Data

US 2019/0110686 A1    Apr. 18, 2019

Related U.S. Application Data

(63) Continuation of application No. PCT/JP2016/069786, filed on Jul. 4, 2016.

(51) Int. Cl.
*A61B 5/00* (2006.01)
*A61B 1/04* (2006.01)
(Continued)

(52) U.S. Cl.
CPC ........ *A61B 5/0071* (2013.01); *A61B 1/00006* (2013.01); *A61B 1/00009* (2013.01);
(Continued)

(58) Field of Classification Search
CPC ............ A61B 1/00006; A61B 1/00009; A61B 1/00096; A61B 1/00186; A61B 1/043;
(Continued)

(56) References Cited

U.S. PATENT DOCUMENTS 6,061,591 A * 5/2000 Freitag ................. A61B 5/0071
600/476
7,062,311 B1 * 6/2006 Sendai ................. A61B 5/0071
250/458.1
(Continued)

FOREIGN PATENT DOCUMENTS

EP    1 227 686 A1    7/2002
JP    2001-78952 A    3/2001
(Continued)

OTHER PUBLICATIONS

International Search Report dated Sep. 20, 2016, issued in counterpart International Application No. PCT/JP2016/069786, w/English translation (4 pages).

*Primary Examiner* — Michael J Carey
*Assistant Examiner* — Julianna J Nicolaus
(74) *Attorney, Agent, or Firm* — WHDA, LLP

(57) ABSTRACT

A light source device configured to irradiate an object with visible light and excitation light, an imaging device including a first substrate on which a plurality of first photoelectric conversion elements configured to detect a visible light within reflected light from the object are formed, a second substrate on which a plurality of second photoelectric conversion elements configured to detect light of an infrared region within the reflected light transmitted through the first substrate are formed, and an interlayer filter configured to attenuate the light of the visible region transmitted through the first substrate, and a setting device configured to set a light emission intensity of the visible light radiated by the light source device so that first photoelectric conversion elements is able to detect the visible light and a detection value of light detected by second photoelectric conversion element become less than or equal to a predetermined value.

13 Claims, 8 Drawing Sheets

(51) Int. Cl.
  *A61B 1/00* (2006.01)
  *A61B 1/05* (2006.01)
  *A61B 5/07* (2006.01)
  *H04N 5/225* (2006.01)
  *H04N 5/33* (2006.01)
  *H04N 9/04* (2006.01)
  *A61B 1/06* (2006.01)
  *G01N 21/64* (2006.01)

(52) U.S. Cl.
  CPC ...... *A61B 1/00096* (2013.01); *A61B 1/00186* (2013.01); *A61B 1/043* (2013.01); *A61B 1/051* (2013.01); *A61B 1/0638* (2013.01); *A61B 5/0062* (2013.01); *A61B 5/07* (2013.01); *A61B 5/6846* (2013.01); *G01N 21/6456* (2013.01); *H04N 5/2256* (2013.01); *H04N 5/332* (2013.01); *H04N 9/045* (2013.01); *H04N 2005/2255* (2013.01)

(58) Field of Classification Search
  CPC ..... A61B 1/051; A61B 1/0638; A61B 1/0669; A61B 5/0086; A61B 5/0071; A61B 5/6846
  See application file for complete search history.

(56) References Cited

U.S. PATENT DOCUMENTS

| | | | |
|---|---|---|---|
| 2002/0196337 A1* | 12/2002 | Takeyama | A61B 1/0646 348/131 |
| 2004/0186351 A1* | 9/2004 | Imaizumi | A61B 5/0071 600/160 |
| 2005/0231720 A1* | 10/2005 | Goto | G03B 13/36 356/399 |
| 2012/0268573 A1* | 10/2012 | Schonborn | G02B 21/16 348/49 |
| 2014/0194748 A1* | 7/2014 | Yamamoto | A61B 5/489 600/473 |

FOREIGN PATENT DOCUMENTS

| | | |
|---|---|---|
| JP | 2006-122335 A | 5/2006 |
| JP | 3962122 B2 | 8/2007 |
| JP | 2014-135535 A | 7/2014 |
| JP | 2015-99875 A | 5/2015 |

* cited by examiner

FLUORESCENCE OBSERVATION DEVICE AND FLUORESCENCE OBSERVATION ENDOSCOPE DEVICE

This application is a continuation application based on PCT Patent Application No. PCT/JP 2016/069786, filed Jul. 4, 2016.

TECHNICAL FIELD

The present invention relates to a fluorescence observation device and a fluorescence observation endoscope device.

BACKGROUND ART

A diagnostic method of determining the presence or absence of a lesion by previously administering a derivative-labeled antibody (fluorescent drug) called indocyanine green (ICG) to a body of a person to be examined in order to diagnose cancer or the like is conventionally known. ICG is a fluorescent material having affinity for a lesion such as cancer and is excited by light of an infrared region and emits fluorescence. Conventionally, various medical systems having a function of allowing observation of the fluorescence emission of ICG have been proposed. Also, for example, an examiner such as a doctor determines the presence or absence of a lesion from the brightness of fluorescence observed using a medical system.

In a conventional medical system, a fluorescence observation device for radiating light of an infrared region such as near-infrared light as excitation light for exciting ICG and imaging a specific protein of a lesion portion emitting fluorescence according to the radiated excitation light is provided as a configuration for observing fluorescence emission.

For example, an endoscope device capable of allowing observation of fluorescence to be performed using excitation light in addition to normal observation using visible light is disclosed in Japanese Patent No. 3962122. In the endoscope device disclosed in Japanese Patent No. 3962122, visible light and excitation light are radiated from a distal end of an insertion unit to an object to be examined and the visible light and the excitation light reflected from the object to be examined and fluorescence emitted by ICG according to excitation due to excitation light are guided to a camera head via an image guide fiber. In the endoscope device disclosed in Japanese Patent No. 3962122, visible light, excitation light, and fluorescence guided to the camera head are first separated into visible light, and excitation light and fluorescence by a dichroic mirror provided within the camera head. The visible light separated here is imaged by an imaging means. Also, in the endoscope device disclosed in Japanese Patent No. 3962122, the excitation light in the separated excitation light and fluorescence is removed (cut) by an excitation light cut filter provided within the camera head and only the fluorescence is intensified by an image intensifier and imaged by an imaging means different from the imaging means for the visible light.

However, in the configuration of the endoscope device disclosed in Japanese Patent No. 3962122, i.e., in the configuration in which light is separated by a dichroic mirror, imaging of visible light and imaging of fluorescence can be simultaneously performed by imaging means, but a size of a configuration of an imaging system, i.e., the imaging unit including the dichroic mirror, the imaging means, or the like, may be increased. Thus, it is difficult to mount a configuration of the imaging unit disclosed in Japanese Patent No. 3962122 on the distal end of the insertion unit of the endoscope device. More specifically, endoscope devices include a type of device in which the imaging unit is mounted outside the insertion unit of the endoscope device and a type of device in which the imaging unit is mounted on the distal end of the insertion unit. In a type of endoscope device in which the imaging unit is mounted on the distal end of the insertion unit, it is possible to perform observation in a wide range by configuring the distal end of the insertion unit on which the imaging unit is mounted so that the distal end of the insertion unit is bent. However, according to the technology of the endoscope device disclosed in Japanese Patent No. 3962122, it is difficult to implement a function of performing observation in a wide range according to a configuration in which the distal end is bent.

Also, for example, as disclosed in Japanese Unexamined Patent Application, First Publication No. 2014-135535, conventionally, a laminated imaging device in which a first substrate for imaging light of a visible region (visible light) and a second substrate for imaging light of an infrared region (near-infrared light) are laminated has been proposed. Japanese Unexamined Patent Application, First Publication No. 2014-135535 discloses technology for mounting a laminated imaging device on an endoscope device. In the endoscope device disclosed in Japanese Unexamined Patent Application, First Publication No. 2014-135535, visible light and excitation light are radiated from the distal end of the endoscope scope unit to the object to be examined and the visible light and the excitation light reflected from the object to be examined and fluorescence emitted by ICG according to excitation due to excitation light are guided to an imaging unit via an image guide. In the endoscope device disclosed in Japanese Unexamined Patent Application. First Publication No. 2014-135535, only the excitation light within the visible light, the excitation light, and the fluorescence is removed (cut) by an excitation light cut filter provided within the camera head and the visible light and the fluorescence are incident on the laminated imaging device. In the laminated imaging device disclosed in Japanese Unexamined Patent Application, First Publication No. 2014-135535, the visible light is imaged in a first substrate, the visible light within the visible light and the fluorescence transmitted through the first substrate is removed (cut) by an interlayer filter arranged between the first substrate and the second substrate, and only the fluorescence is imaged in the second substrate.

Although Japanese Unexamined Patent Application, First Publication No. 2014-135535 discloses a configuration of an endoscope device including a laminated imaging device in an imaging unit, the implementation of an endoscope device in which a size of a distal end is reduced by mounting the laminated imaging device as disclosed in Japanese Unexamined Patent Application, First Publication No. 2014-135535 on the distal end of the endoscope device is also conceived.

However, the emission of fluorescence by ICG is significantly weak. Thus, in the laminated imaging device as disclosed in Japanese Unexamined Patent Application, First Publication No. 2014-135535 (hereinafter referred to as a "laminated image sensor"), it is necessary to remove (cut) visible light transmitted through the first substrate at a significantly high light shielding rate in the interlayer filter arranged between the first substrate and the second substrate so as to image weak fluorescence due to ICG in the second substrate and sufficiently decrease an intensity of visible light as compared with an intensity of fluorescence. However, it is difficult to sufficiently remove (cut) the visible light transmitted through the first substrate because the light shielding rate of visible light is significantly low when an organic material similar to that of an on-chip color filter attached to the first substrate for separating the visible light into light of wavelength bands of red (R), green (G), and blue (B) and causing the separated light to be incident is used as a material of the interlayer filter to be arranged in the laminated image sensor.

Therefore, a multilayer film interference filter obtained by laminating inorganic materials on multiple layers may be used as an interlayer filter. In a multilayer film interference filter, it is possible to increase a light shielding rate by increasing the number of laminated films. However, the multilayer film interference filter may increase the thickness of the filter by increasing the number of films to be laminated. Then, when a thick multilayer film interference filter having a large thickness obtained by increasing the number of films to be laminated until a sufficient high light shielding rate can be implemented is arranged in the laminated image sensor, the distance between a microlens arranged on the first substrate and the second substrate may be lengthened and a sensitivity to light in pixels arranged on the second substrate or characteristics for light incident in an oblique direction (an oblique incidence characteristic) may significantly deteriorate.

Thus, when a laminated image sensor is actually mounted on the distal end of an endoscope device, it is necessary to arrange a thin multilayer film interference filter (which is not extremely thick), i.e., a multilayer film interference filter, as an interlayer filter between the first substrate and the second substrate of the laminated image sensor in which a sufficiently high light shielding rate cannot be implemented, and implement measures for compensating for a decrease in the light shielding rate of the interlayer filter.

As the measure for compensating for a decrease in the light shielding rate of the interlayer filter, a method of minimizing an intensity of visible light to be radiated from the distal end of the endoscope device to an object to be examined can be conceived. In order to prevent erroneous detection of fluorescence (the deterioration of detection accuracy of fluorescence) in any situation in the endoscope device in this method, the intensity of visible light radiated to the object to be examined is determined to be the intensity at which it is possible to compensate for a decrease in the light shielding rate of the interlayer filter even in a situation in which an intensity of visible light reflected from the object to be examined is high, i.e., a situation in which the reflectance of visible light on the object to be examined is high and the distance between the distal end of the endoscope device and the object to be examined is short. Thus, the intensity of the visible light radiated to the object to be examined is set to a sufficiently minimized (weakened) intensity so that it is possible to compensate for the visible light which cannot be removed (cut) by the interlayer filter in any situation. Also, considering that the visible light reflected from the object to be examined varies with the reflectance of the visible light on the object to be examined, the intensity of the visible light to be radiated to the object to be examined is set to a further minimized (weakened) intensity when assuming that the reflectance of visible light of the object to be examined is high.

However, if the intensity of the visible light to be radiated on the object to be examined is set to a sufficiently minimized (weakened) intensity for example, the visible light incident on the first substrate of the laminated image sensor is significantly decreased under a situation in which the intensity of the visible light reflected from the object to be examined is weak such as a situation in which the reflectance of the object to be examined is low or a situation in which the distance between the distal end of the endoscope device and the object to be examined is long. A decrease in visible light incident on the first substrate of the laminated image sensor becomes a cause of the quality of an image including the object to be examined imaged in the first substrate deteriorating.

SUMMARY OF INVENTION

Solution to Problem

According to a first aspect of the present invention, there is provided a fluorescence observation device, including: a light source device configured to irradiate an object with light including wavelength bands of visible light and excitation light; an imaging device including a first substrate on which a plurality of first photoelectric conversion elements are formed, a second substrate on which a plurality of second photoelectric conversion elements are formed, and an interlayer filter arranged between the first substrate and the second substrate, the first photoelectric conversion element being configured to detect light of a visible region within reflected light reflected from the object, the second photoelectric conversion element being configured to detect light of an infrared region within the reflected light transmitted through the first substrate, and the interlayer filter being configured to attenuate the light of the visible region transmitted through the first substrate; and a setting device configured to set a light emission intensity of the visible light radiated by the light source device so that each first photoelectric conversion elements is able to detect the visible light and a detection value of light detected by each second photoelectric conversion element become less than or equal to a predetermined value.

According to a second aspect of the present invention, in the fluorescence observation device according to the above-described first aspect, the light source device may be configured to independently set the light emission intensity of the visible light and light emission intensity of the excitation light and the setting device may be configured to set the light emission intensity of the visible light irradiated by the light source device on the basis of a first detection intensity which is an intensity of light of the visible region included in the reflected light detected by each first photoelectric conversion element.

According to a third aspect of the present invention, in the fluorescence observation device according to the above-described second aspect, when the first detection intensity detected by one of the first photoelectric conversion elements exceeds a preset maximum detection intensity, the setting device may be configured to set the light emission intensity of the visible light so that the first detection intensity detected by each first photoelectric conversion element becomes less than or equal to the maximum detection intensity.

According to a fourth aspect of the present invention, in the fluorescence observation device according to the above-described third aspect, the setting device may be configured to set the light emission intensity of the visible light at a timing synchronized with a cycle in which each first photoelectric conversion element detects the first detection intensity.

According to a fifth aspect of the present invention, in the fluorescence observation device according to the above-described fourth aspect, the setting device may be configured to monitor a second detection intensity while gradually changing the light emission intensity of the visible light, the setting device may be configured to store a level of the first detection intensity detected by the corresponding first photoelectric conversion element when a level of the second detection intensity has been changed by an amount greater than or equal to a predetermined value, and the second detection intensity is an intensity of light detected by each second photoelectric conversion element, the setting device may be configured to set the maximum detection intensity on the basis of the stored level of the first detection intensity.

According to a sixth aspect of the present invention, in the fluorescence observation device according to the above-described fifth aspect, the first photoelectric conversion element may correspond to light of a visible region of any one of a visible region of a first wavelength band, a second wavelength band, and a third wavelength band, the first wavelength band is wavelength band from light of a visible region, the second wavelength band is wavelength band of a visible region and different from the first wavelength band, the third wavelength band is wavelength band of a visible region and different from both of the first wavelength band and the second wavelength band, the setting device may be configured to store a minimum level of the first detection intensity for each of the wavelength band corresponding to the first photoelectric conversion element, and the setting device may be configured to set the maximum detection intensity corresponding to each of the visible region of the first wavelength band, the visible region of the second wavelength band, and the visible region of the third wavelength band on the basis of each stored minimum level of the first detection intensity.

According to a seventh aspect of the present invention, in the fluorescence observation device according to the above-described second aspect, the setting device may be configured to set the light emission intensity of the visible light so that the first detection intensity becomes a preset intensity.

According to an eighth aspect of the present invention, in the fluorescence observation device according to the above-described seventh aspect, the setting device may be configured to set the light emission intensity of the visible light at a timing synchronized with a cycle in which each first photoelectric conversion element detects the first detection intensity.

According to a ninth aspect of the present invention, in the fluorescence observation device according to the above-described eighth aspect, the setting device may be configured to monitor a second detection intensity while gradually changing the light emission intensity of the visible light, the setting device may be configured to store a level of the first detection intensity detected by the corresponding first photoelectric conversion element when a level of the second detection intensity has been changed by an amount greater than or equal to a predetermined value, and the second detection intensity is an intensity of light detected by each second photoelectric conversion element, the setting device may be configured to set the fixed detection intensity on the basis of the stored level of the first detection intensity.

According to a tenth aspect of the present invention, in the fluorescence observation device according to the above-described ninth aspect, the first photoelectric conversion element may correspond to light of a visible region of any one of a visible region of a first wavelength band, a second wavelength band, and a third wavelength band, the first wavelength band is wavelength band from light of a visible region, the second wavelength band is wavelength band of a visible region and different from the first wavelength band, the third wavelength band is wavelength band of a visible region and different from both of the first wavelength band and the second wavelength band, the setting device may be configured to store a minimum level of the first detection intensity for each of the wavelength band corresponding to the first photoelectric conversion element, and the setting device may be configured to set the fixed detection intensity corresponding to each of the visible region of the first wavelength band, the visible region of the second wavelength band, and the visible region of the third wavelength band on the basis of each stored minimum level of the first detection intensity.

According to an eleventh aspect of the present invention, in the fluorescence observation device according to the above-described first aspect, the interlayer filter may be a dielectric multilayer film filter.

According to a twelfth aspect of the present invention, there is provided a fluorescence observation endoscope device for observing a fluorescent material, including: a fluorescence observation device which includes a light source device configured to irradiate an object to be examined with light including wavelength bands of visible light and excitation light for causing the object to be examined to emit fluorescence by irradiating the fluorescent material with light, an imaging device including a first substrate on which a plurality of first photoelectric conversion elements are formed, a second substrate on which a plurality of second photoelectric conversion elements are formed, and an interlayer filter arranged between the first substrate and the second substrate, the first photoelectric conversion element being configured to detect light of a visible region within reflected light reflected from the object to be examined, the second photoelectric conversion element being configured to detect the fluorescence within the reflected light transmitted through the first substrate, and the interlayer filter being configured to attenuate the light of the visible region transmitted through the first substrate; and a setting device configured to set a light emission intensity of the visible light radiated by the light source device so that each first photoelectric conversion elements is able to detect the visible light and a detection value of the fluorescence detected by each second photoelectric conversion element become less than or equal to a predetermined value.

According to a thirteenth aspect of the present invention, in the fluorescence observation device according to the above-described twelfth aspect, the imaging device may be arranged at a distal end of an insertion unit of the fluorescence observation endoscope device to be inserted into a living body.

DESCRIPTION OF EMBODIMENTS

Figure 1:
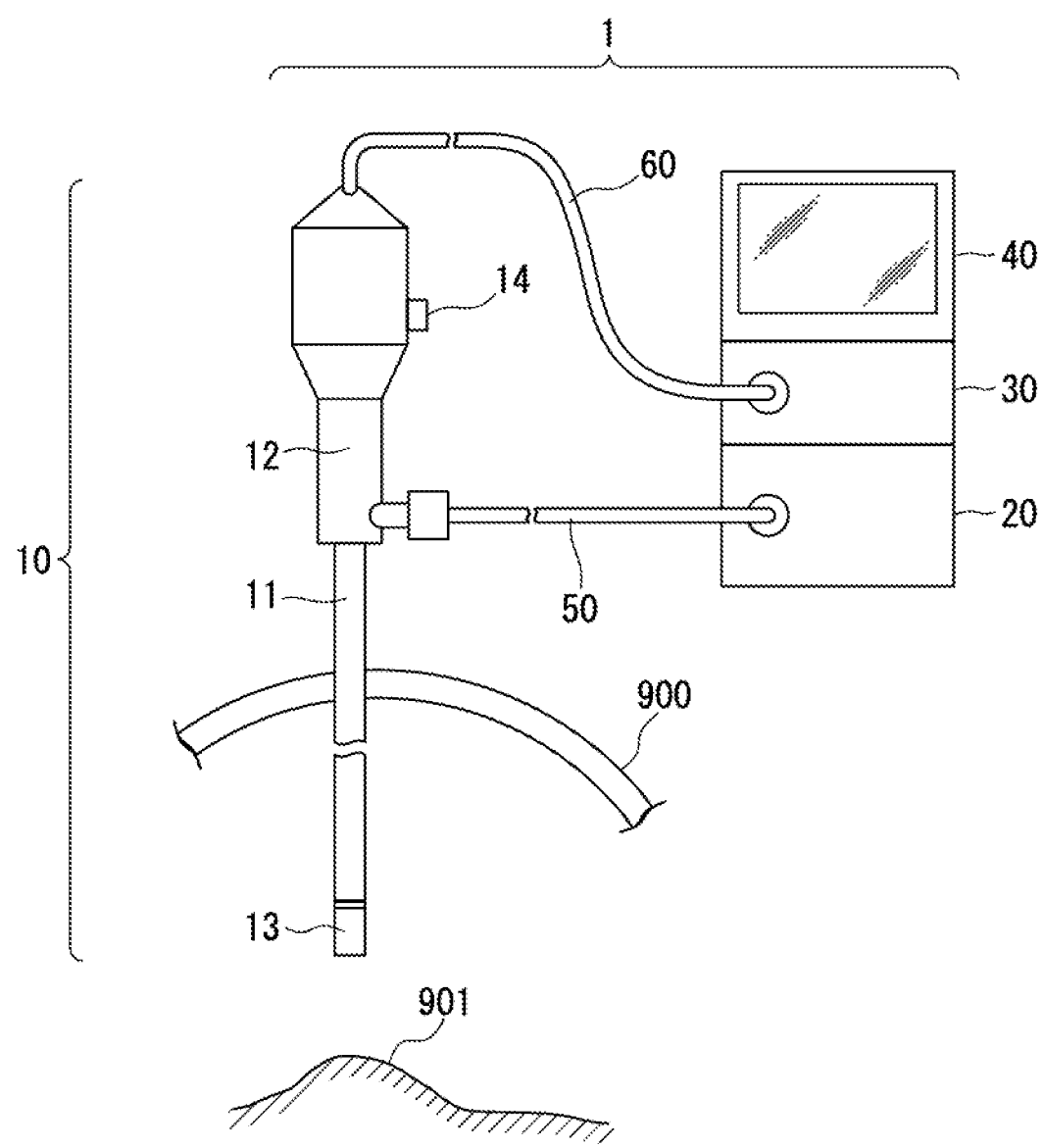
FIG. 1 is a configuration diagram showing a schematic configuration of a fluorescence observation endoscope device according to an embodiment of the present invention.

Hereinafter, embodiments of the present invention will be described with reference to the drawings. In the following description, a case in which a fluorescence observation device of the present invention is configured as a fluorescence observation endoscope device will be described. FIG. 1 is a configuration diagram showing a schematic configuration of the fluorescence observation endoscope device according to an embodiment of the present invention.

In FIG. 1, a fluorescence observation endoscope device 1 includes an endoscope scope unit 10, a light source device 20, an external processing unit 30, and a color monitor 40. The fluorescence observation endoscope device 1 is, for example, an endoscope device for laparoscopic surgery. In the fluorescence observation endoscope device 1, an insertion unit of the endoscope scope unit 10 to be inserted into a body is inserted into an abdominal portion 900 of a person to be examined and an object 901 to be examined which is an observation object such as living tissue within the body of the person to be examined is photographed. In FIG. 1, a state in which the insertion unit of the endoscope scope unit 10 constituting the fluorescence observation endoscope device 1 is inserted into the abdominal portion 900 of the person to be examined and the object 901 is photographed is shown.

The fluorescence observation endoscope device 1 is used for the person to be examined in a state in which a derivative labeled antibody (fluorescent drug) such as ICG or the like has been administered to the body in advance. In the following description, an example in which ICG is administered as a fluorescent drug to the body of the person to be examined will be described.

The fluorescence observation endoscope device 1 performs photographing of the object 901 using visible light (hereinafter referred to as "normal photographing") and photographing of the object 901 using fluorescence emitted through excitation of ICG administered by radiating excitation light such as near-infrared light (hereinafter referred to as "fluorescence photographing").

In the fluorescence observation endoscope device 1, the endoscope scope unit 10 includes an insertion unit 11 and an operation unit 12. In the fluorescence observation endoscope device 1, the operation unit 12 of the endoscope scope unit 10 and a light source device 20 are connected by a light signal cable 50. In the fluorescence observation endoscope device 1, the operation unit 12 of the endoscope scope unit 10 and an external processing unit 30 are connected by an electrical signal cable 60.

In the endoscope scope unit 10, the insertion unit 11 is inserted into the abdominal portion 900 or the like of the person to be examined, and captures an image of the object 901. At this time, illumination light guided through the light signal cable 50 is radiated from a distal end of the insertion unit 11 to the object 901. The endoscope scope unit 10 outputs an imaging signal corresponding to the captured image of the object 901 to the external processing unit 30 via the electrical signal cable 60.

The insertion unit 11 is inserted into the body of the person to be examined from the abdominal portion 900 of the person to be examined in a state in which ICG has been administered in advance. In the endoscope scope unit 10, the insertion unit 11 includes an imaging unit 13 on the distal end thereof. The imaging unit 13 generates an imaging signal obtained by converting an image of the object 901 into an electrical signal. Then, the imaging unit 13 outputs the generated imaging signal to the external processing unit 30 via the insertion unit 11, the operation unit 12, and the electrical signal cable 60.

The operation unit 12 is a support unit configured to control operations of the insertion unit 11 and the imaging unit 13, for example, when an examiner (for example, a doctor who performs laparoscopic surgery) operates the operation unit 12. In the endoscope scope unit 10, the operation unit 12 includes a photographing control switch 14 configured to control photographing in the fluorescence observation endoscope device 1. For example, the photographing control switch 14 outputs a control signal for issuing an instruction for photographing (the normal photographing or the fluorescence photographing) to the external processing unit 30 via the operation unit 12 and the electrical signal cable 60, for example, in accordance with an operation of the examiner.

The light source device 20 emits illumination light to be radiated to the object 901 when the object 901 is observed in the fluorescence observation endoscope device 1. The illumination light emitted from the light source device 20 is guided to the operation unit 12 of the endoscope scope unit 10 via the light signal cable 50 and radiated from the imaging unit 13 provided on the distal end of the insertion unit 11 to the object 901. The light source device 20 emits illumination light of a wavelength band used for photographing the object 901 in the fluorescence observation endoscope device 1. More specifically, the light source device 20 emits the illumination light including the visible light to be used by the fluorescence observation endoscope device 1 to perform the normal photographing of the object 901 and the fluorescence to be used by the fluorescence observation endoscope device 1 to perform the fluorescence photographing of the object 901.

The external processing unit 30 is an image processing device configured to perform predetermined image processing on the imaging signal of the object 901 photographed by the imaging unit 13 provided in the endoscope scope unit 10 input via the electrical signal cable 60 and generate an image including the photographed object 901. The external processing unit 30 outputs an image signal of the generated image including the object 901 to the color monitor 40 and causes the color monitor 40 to display an image. Also, the external processing unit 30 transmits a control signal (a driving signal) when the imaging unit 13 photographs the object 901 to the imaging unit 13 via the electrical signal cable 60.

The color monitor 40 is, for example, a display device, such as a liquid crystal display (LCD), configured to display an image including the object 901 according to the image signal input from the external processing unit 30.

According to such a configuration, the fluorescence observation endoscope device 1 performs the normal photographing of the object 901 with visible light and the fluorescence photographing of the object 901 with fluorescence obtained through excitation of ICG administered to the person to be examined by excitation light. Then, the fluorescence observation endoscope device 1 presents the image including the photographed object 901 to the examiner.

Figure 2:
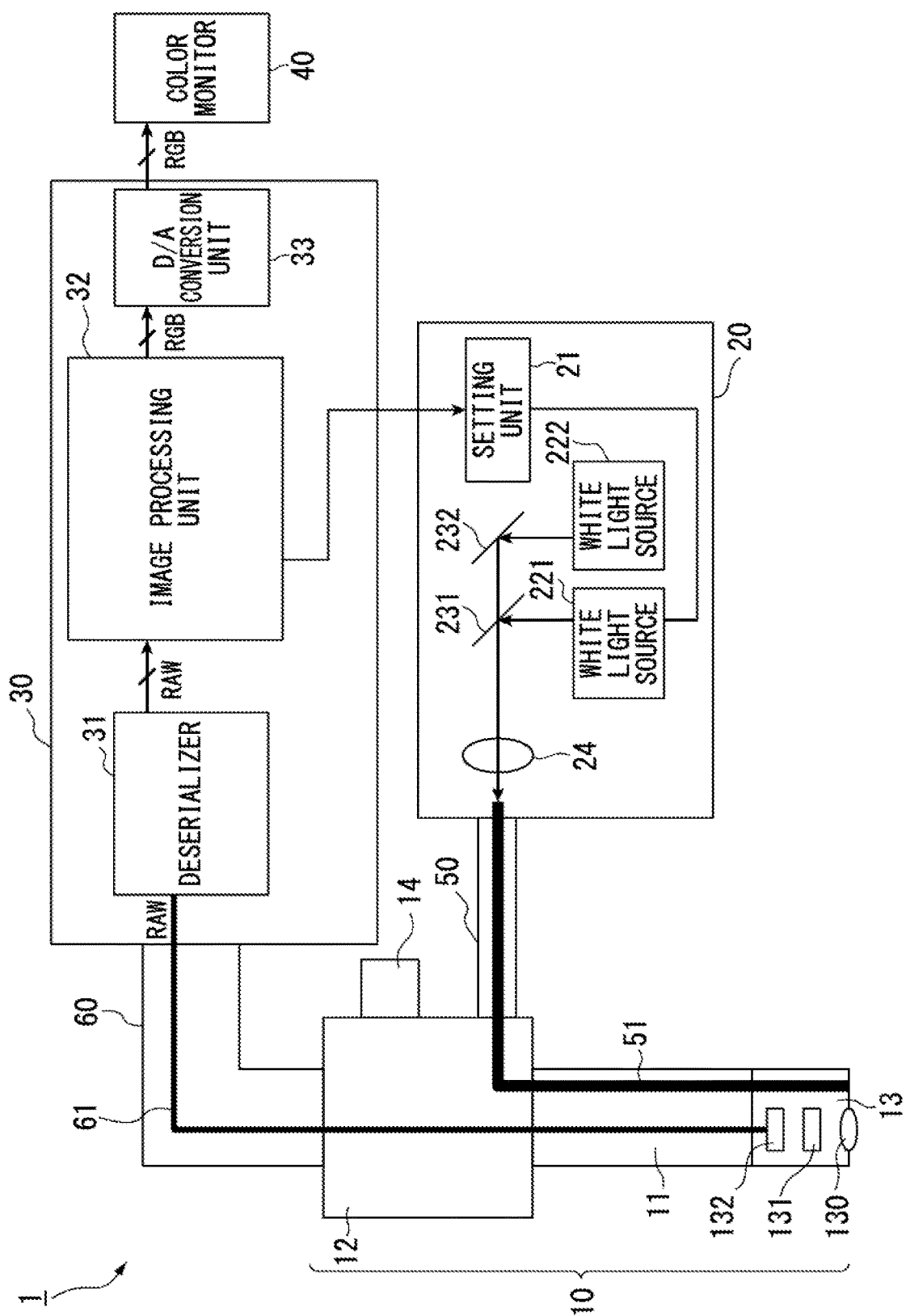
FIG. 2 is a block diagram showing a schematic configuration of the fluorescence observation endoscope device according to the embodiment of the present invention.

Next, a more detailed configuration of the fluorescence observation endoscope device 1 will be described. FIG. 2 is a block diagram showing a schematic configuration of the fluorescence observation endoscope device 1 according to the embodiment of the present invention. In FIG. 2, the imaging unit 13 provided on the distal end of the endoscope scope unit 10 constituting the fluorescence observation endoscope device 1 includes an imaging lens 130, an excitation light cut filter 131, a laminated image sensor 132, and a light guide 51.

The light guide 51 is, for example, a light guide cable, such as an optical fiber, configured to guide the illumination light emitted by the light source device 20 to the imaging unit 13. The light guide 51 guides the illumination light emitted by the light source device 20 to the imaging unit 13 through the light signal cable 50, the operation unit 12, and the insertion unit 11 and radiates the illumination light from the distal end of the light guide 51 to the object 901.

The imaging lens 130 is an optical lens configured to emit incident light, i.e., reflected light and fluorescence from the object 901 with which the illumination light has been irradiated by the light source device 20, to the laminated image sensor 132 side and form an image of the object 901 on an imaging plane of the laminated image sensor 132.

The excitation light cut filter 131 is an optical filter configured to reflect or absorb and attenuate only the light of the wavelength band of the excitation light included in the reflected light and the fluorescence from the object 901 emitted from the imaging lens 130. For example, the excitation light cut filter 131 attenuates light of a wavelength band in the vicinity of 700 nm to 800 nm which is the wavelength band of the excitation light. Also, in the following description, because the excitation light cut filter 131 attenuates the excitation light included in the incident reflected light and the fluorescence to a level close to nearly "0", description will be given using the term "removal (cut)" instead of "attenuation". The excitation light cut filter 131 emits the reflected light and the fluorescence from the object 901 obtained by cutting the excitation light to the laminated image sensor 132.

The laminated image sensor 132 is a solid-state imaging device configured to allow exposure with (detect) incident light and output an electrical signal obtained by photoelectrically converting the exposure light as an imaging signal. The laminated image sensor 132 allows exposure with the reflected light and fluorescence from the object 901 obtained by cutting the excitation light emitted from the excitation light cut filter 131 and generates imaging signals according to the reflected light and the fluorescence which have been used for exposure. The laminated image sensor 132 is configured to include an image sensor configured to allow exposure with (detect) the reflected light (hereinafter referred to as a "visible-image capturing image sensor"), an image sensor configured to allow exposure with (detect) the fluorescence transmitted through the visible-image capturing image sensor (hereinafter referred to as a "fluorescence-image capturing image sensor"), and an interlayer filter arranged between the visible-image capturing image sensor and the fluorescence-image capturing image sensor. That is, the laminated image sensor 132 has a structure in which the visible-image capturing image sensor and the fluorescence-image capturing image sensor are laminated with the interlayer filter interposed therebetween.

The visible-image capturing image sensor constituting the laminated image sensor 132 outputs an imaging signal obtained by allowing exposure with light of the visible region (visible light) within the reflected light. In the visible-image capturing image sensor, a plurality of pixels each having a photoelectric conversion element (a light-receiving element) such as a photodiode configured to photoelectrically convert incident light are arranged in a matrix shape. Pixels arranged within the visible-image capturing image sensor are a pixel to which an on-chip color filter configured to transmit light (visible light) of a wavelength band of red (R) is attached (hereinafter referred to as an "R pixel"), a pixel to which an on-chip color filter configured to transmit light (visible light) of a wavelength band of green (G) is attached (hereinafter referred to as a "G pixel"), and a pixel to which an on-chip color filter configured to transmit light (visible light) of a wavelength band of blue (B) is attached (hereinafter referred to as a "B pixel").

Also, the interlayer filter constituting the laminated image sensor 132 is an optical filter configured to reflect or absorb and attenuate light of the visible region (visible light) within light transmitted through the visible-image capturing image sensor (more specifically, the regions of R, G and B pixels arranged in the visible-image capturing image sensor). In the laminated image sensor 132, for example, a multilayer film interference filter obtained by laminating inorganic materials such as a dielectric multilayer film filter or a Fabry-Perot filter on multiple layers is used as an interlayer filter. Also, it may be easy to implement an interlayer filter having a characteristic of attenuating light of a wide wavelength band in the dielectric multilayer film filter from a dielectric multilayer film filter and a Fabry-Perot filter. In the following description, an example in which the interlayer filter is a dielectric multilayer film filter will be described.

Also, the fluorescence-image capturing image sensor constituting the laminated image sensor 132 outputs an imaging signal obtained by allowing exposure with fluorescence, i.e., light of the infrared region (near-infrared light). In the fluorescence-image capturing image sensor, a plurality of pixels each including a photoelectric conversion element (a light-receiving element) such as a photodiode configured to photoelectrically convert light transmitted through the visible-image capturing image sensor (more specifically, a region of R, G, and B pixels arranged in the visible-image capturing image sensor) and the interlayer filter are arranged in a matrix shape. In the following description, a pixel arranged in the fluorescence-image capturing image sensor is referred to as a "fluorescent pixel". The fluorescent pixel is a pixel configured to allow exposure with (detect) fluorescence emitted through excitation of ICG administered to a person to be examined according to excitation light such as near-infrared light radiated by the light source device 20.

Also, a detailed description of the structure of the laminated image sensor 132, the arrangement and configuration of each pixel in the visible-image capturing image sensor and the fluorescence-image capturing image sensor, and the structure of the interlayer filter will be described below.

The laminated image sensor 132 outputs an imaging signal (hereinafter referred to as a "visible-image capturing signal") according to an electrical signal (hereinafter referred to as a "pixel signal") obtained by exposing each pixel arranged in the visible-image capturing image sensor and performing photoelectric conversion thereon to the external processing unit 30 through an imaging signal line 61 passing through the insertion unit 11, the operation unit 12, and the electrical signal cable 60. Also, the laminated image sensor 132 outputs an imaging signal according to a pixel signal obtained by exposing each pixel arranged in the fluorescence-image capturing image sensor and performing photoelectric conversion (hereinafter referred to as a "fluorescence-image capturing signal") to the external processing unit 30 through the imaging signal line 61 as in the visible-image capturing signal. In the following description, the visible-image capturing signal and the fluorescence-image capturing signal are simply referred to as "imaging signals" unless they are distinguished from each other.

Also, the laminated image sensor 132 performs analog/digital conversion (A/D conversion) on analog pixel signals output by pixels arranged within the visible-image capturing image sensor and the fluorescence-image capturing image sensor, and outputs digital values representing magnitudes of pixel signals, i.e., so-called RAW data, as imaging signals to the external processing unit 30. The RAW data is parallel digital values representing magnitudes of pixel signals.

In order to reduce the number of signal lines of the imaging signal line 61 for transmitting RAW data as an imaging signal to the external processing unit 30, the laminated image sensor 132 converts RAW data which is parallel digital values (hereinafter referred to as "parallel RAW data") into RAW data of a serial digital value (hereinafter referred to as "serial RAW data") according to serial/parallel conversion, and outputs the serial RAW data as the imaging signal to the external processing unit 30.

Also, in FIG. 2, the light source device 20 constituting the fluorescence observation endoscope device 1 is configured to include a setting unit 21, two white light sources 221 and 222, two dichroic mirrors 231 and 232, and a light irradiation lens 24.

Each of the white light source 221 and the white light source 222 is a light source configured to emit white light. However, the white light source 221 emits white light having an intensity according to control from the setting unit 21. Also, as the white light source 221 and the white light source 222, for example, a xenon lamp is used. However, as the white light source 221 and the white light source 222, for example, a halogen lamp, a white light-emitting diode (LED) light source, or the like may be used. In the following description, the white light source 221 and the white light source 222 are referred to as "white light sources 220" unless they are distinguished from each other.

The dichroic mirror 231 and the dichroic mirror 232 correspond to the white light source 221 and the white light source 222, respectively, and select (separate) light of specific wavelength bands from white light emitted by the corresponding white light sources 220. Each of the dichroic mirror 231 and the dichroic mirror 232 emits the separated light to the light irradiation lens 24.

More specifically, the dichroic mirror 231 emits visible light (white light) separated by reflecting light of a wavelength band of visible light in white light emitted by the corresponding white light source 221 (for example, light of a wavelength band of 400 nm to 700 nm) in a direction in which the light irradiation lens 24 is arranged to the light irradiation lens 24. Here, the visible light emitted to the light irradiation lens 24 by the dichroic mirror 231 includes light of a wavelength band of blue (B) (for example, light in a wavelength band of 400 nm to 500 nm), light of a wavelength band of green (G) (for example, light in a wavelength band of 500 nm to 600 nm), and light of a wavelength band of red (R) (for example, light in a wavelength band of 600 nm to 700 nm). Also, the dichroic mirror 232 emits excitation light (near-infrared light) for exciting ICG separated by reflecting light of an excitation-light wavelength band in white light emitted by the corresponding white light source 222 (for example, light of a wavelength band of 700 nm to 800 nm) in a direction in which the light irradiation lens 24 is arranged to the light irradiation lens 24.

The light irradiation lens 24 is an optical lens configured to concentrate light of a specific wavelength band emitted from each of the dichroic mirror 231 and the dichroic mirror 232 to the same extent as a diameter of the light guide 51. The light irradiation lens 24 emits the concentrated light to a first end surface of the light guide 51. Thereby, the light guide 51 guides the light emitted from the light irradiation lens 24 to the imaging unit 13 and emits light from a second end surface arranged on a distal end of the imaging unit 13 (radiates the light to the object 901) as illumination light emitted by the light source device 20.

The setting unit 21 controls an intensity of white light emitted by the white light source 221 on the basis of digital values (parallel RAW data) representing magnitudes of pixel signals included in the visible-image capturing signal and the fluorescence-image capturing signal input from the external processing unit 30. Also, a detailed description of control of a light emission intensity of the white light source 221 based on the parallel RAW data in the setting unit 21 will be described below.

Also, in FIG. 2, the external processing unit 30 constituting the fluorescence observation endoscope device 1 is configured to include a deserializer 31, an image processing unit 32, and a digital/analog conversion unit (D/A conversion unit) 33.

The deserializer 31 restores the original parallel RAW data obtained by the laminated image sensor 132 performing the analog/digital conversion from the imaging signal (the serial RAW data) output from the laminated image sensor 132 provided in the imaging unit 13 and transmitted through the imaging signal line 61. That is, the deserializer 31 restores the parallel RAW data by performing serial/parallel conversion on the input serial RAW data. Then, the deserializer 31 outputs the restored parallel RAW data to the image processing unit 32.

The image processing unit 32 generate an image of digital values including the object 901 imaged by the laminated image sensor 132 by performing image processing on parallel RAW data output from the deserializer 31. More specifically, the image processing unit 32 generates a visible image of digital values of red (R), green (G), and blue (B) visible light based on the parallel RAW data of the visible-image capturing signal. Also, the image processing unit 32 generates a fluorescence image of the digital values of fluorescence based on the parallel RAW data of the fluorescence-image capturing signal. The image processing unit 32 outputs data of the generated visible image and data of the generated fluorescence image including the object 901 as image data for display (hereinafter referred to as "display image data") to the digital/analog conversion unit 33.

Also, the image processing unit 32 outputs the parallel RAW data (the parallel RAW data of the visible-image capturing signal and the fluorescence-image capturing signal) output from the deserializer 31 as a monitoring signal for setting the intensity of white light to the setting unit 21 provided in the light source device 20. That is, the image processing unit 32 outputs a digital value representing the magnitude of the pixel signal output by each pixel arranged within the visible-image capturing image sensor and the fluorescence-image capturing image sensor provided in the laminated image sensor 132 as a monitoring signal to the setting unit 21.

Also, examples of the image processing performed on the parallel RAW data by the image processing unit 32 include a demosaicing process, a white balance process, a gamma correction process, and the like. The demosaicing process is image processing similar to a so-called triplication process of generating image data indicated by a pixel signal (a digital value) according to light of the same wavelength band in all pixels included in the image on the basis of input parallel RAW data (restored parallel RAW data). The white balance process is image processing for adjusting a level by multiplying a digital value of each pixel by a gain value so that magnitudes of digital values of pixel signals corresponding to pixels of the same position in image data are similar with respect to a white object. The gamma correction process is image processing for correcting color non-linearity of an image signal of an image to be output and an image to be actually displayed on the color monitor 40 when an image according to image data subjected to the white balance process is output to the color monitor 40 for display.

For example, the image processing unit 32 outputs the image data processed until the gamma correction process as display image data to the digital/analog conversion unit 33. Also, for example, the image processing unit 32 may output image data obtained by performing a superimposition process of superimposing image data of a visible image processed until the gamma correction process on image data of a fluorescence image processed until the gamma correction process as display image data to the digital/analog conversion unit 33. Also, for example, the image processing unit 32 may output image data of the visible image and the fluorescence image processed until the demosaicing process as a monitoring signal for setting the intensity of the white light to the setting unit 21 provided in the light source device 20.

The digital/analog conversion unit 33 performs digital/analog conversion (D/A conversion) on display image data (digital values) input from the image processing unit 32. The digital/analog conversion unit 33 outputs an image signal (an analog signal) obtained by performing the digital/analog conversion to the color monitor 40 as a display image signal generated by the external processing unit 30 and causes the color monitor 40 to display an image including the object 901.

According to such a configuration, the fluorescence observation endoscope device 1 captures an image including the object 901 according to the normal photographing using visible light and the fluorescence photographing using fluorescence. Then, the fluorescence observation endoscope device 1 displays each image including the photographed object 901 on the color monitor 40 and presents the displayed image to the examiner.

Also, in the fluorescence observation endoscope device 1, the excitation light cut filter 131 and the laminated image sensor 132 within the imaging unit 13 provided on the distal end of the endoscope scope unit 10, the light source device 20, and the image processing unit 32 provided in the external processing unit 30 correspond to components constituting the fluorescence observation device of the present invention.

Figure 3:
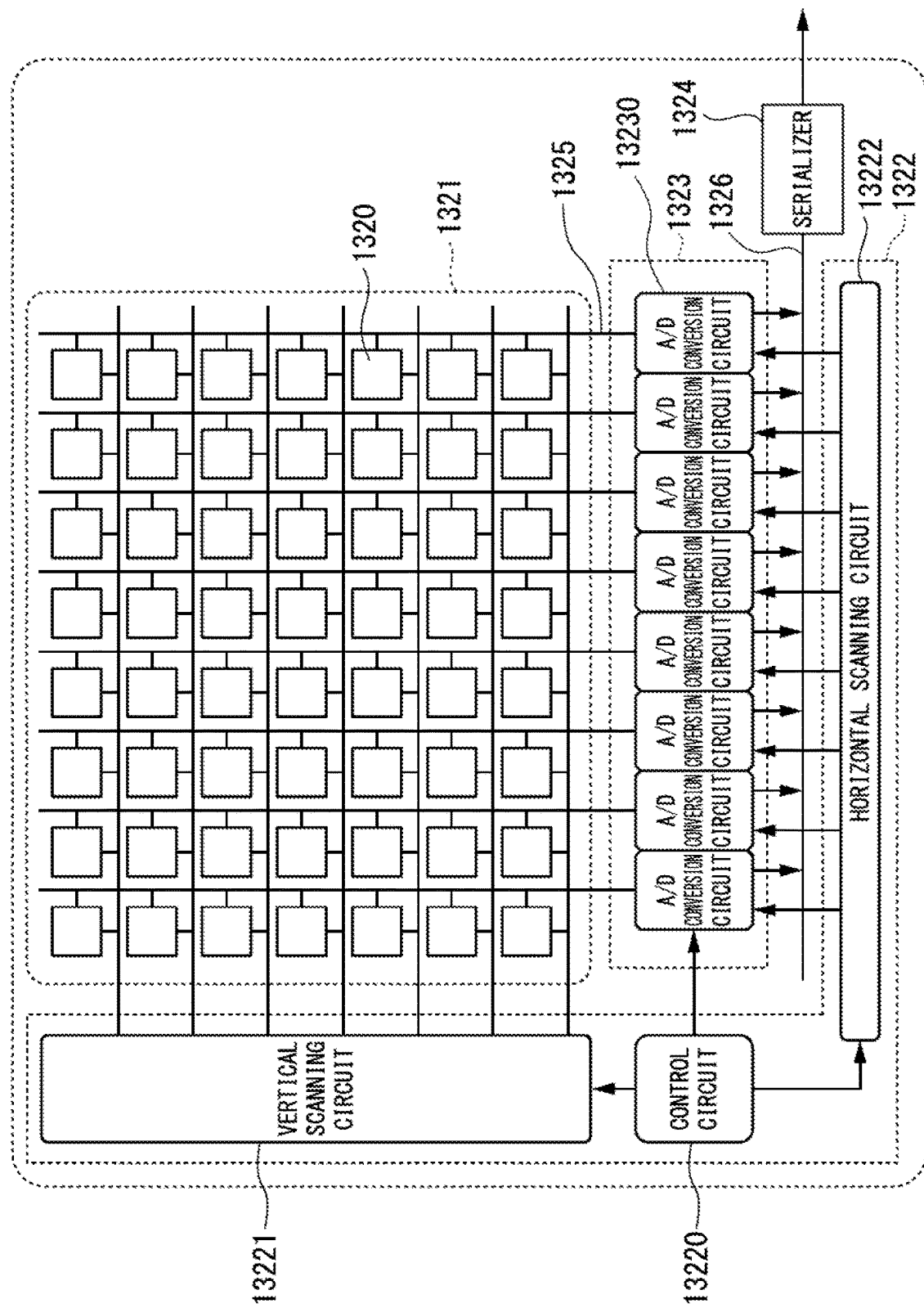
FIG. 3 is a block diagram showing a schematic configuration of a solid-state imaging device provided in the fluorescence observation endoscope device according to the embodiment of the present invention.

Next, the laminated image sensor 132 constituting the fluorescence observation device of the present invention in the fluorescence observation endoscope device 1 will be described. First, a configuration of the visible-image capturing image sensor and the fluorescence-image capturing image sensor constituting the laminated image sensor 132 will be described. FIG. 3 is a block diagram showing a schematic configuration of a solid-state imaging device (the laminated image sensor 132) provided in the fluorescence observation endoscope device 1 according to the embodiment of the present invention. Also, although two image sensors (solid-state imaging devices), i.e., the visible-image capturing image sensor and the fluorescence-image capturing image sensor, are laminated in the laminated image sensor 132, the configurations of the image sensors are similar to each other. In the following description, the configuration of the visible-image capturing image sensor will be described as a representative of image sensors laminated on the laminated image sensor 132.

In FIG. 3, the visible-image capturing image sensor includes a pixel unit 1321, a reading unit 1322, an analog/digital conversion unit 1323, and a serializer 1324.

In the pixel unit 1321, a plurality of pixels 1320 are arranged. In FIG. 3, an example of the pixel unit 1321 in which the plurality of pixels 1320 are two-dimensionally arranged in 7 rows and 8 columns is shown. Each of the pixels 1320 arranged within the pixel unit 1321 generates signal charges of the amount of charge according to an intensity of light incident at each arrangement position and stores the generated signal charges.

The reading unit 1322 controls reading of signal charges generated and stored in each pixel 1320 arranged within the pixel unit 1321. The reading unit 1322 is configured to include, for example, a control circuit 13220, a vertical scanning circuit 13221, a horizontal scanning circuit 13222, and the like. The control circuit 13220 controls the components provided in the reading unit 1322, i.e., the whole of the reading unit 1322. The vertical scanning circuit 13221 drives the pixels 1320 within the pixel unit 1321 row by row in accordance with the control from the control circuit 13220 and causes a voltage signal corresponding to the signal charges stored in each pixel 1320 to be output as the pixel signal to the vertical signal line 1325. Thereby, pixel signals (analog signals) output by the pixels 1320 for each row are input to the analog/digital conversion unit 1323. The horizontal scanning circuit 13222 controls the analog/digital conversion unit 1323 for each column of pixels 1320 within the pixel unit 1321 in accordance with control from the control circuit 13220 and the analog/digital conversion unit 1323 causes pixel signals (digital values) after the analog/digital conversion is performed to be sequentially output to the horizontal signal line 1326 for each column of the pixels 1320 within the pixel unit 1321. Thereby, pixel signals of digital values representing magnitudes of analog pixel signals output by the pixels 1320 after the analog/digital conversion unit 1323 performs the analog/digital conversion are sequentially input to the serializer 1324 for each column of the pixels 1320 arranged in the pixel unit 1321.

The analog/digital conversion unit 1323 performs analog/digital conversion on the analog pixel signals output from the pixels 1320 within the pixel unit 1321 in accordance with control from the vertical scanning circuit 13221 within the reading unit 1322. In FIG. 3, an example of the analog/digital conversion unit 1323 in which an analog/digital conversion circuit (A/D conversion circuit) 13230 configured to output a digital value obtained by performing analog/digital conversion on a voltage value of an input analog signal is provided for each column of the pixels 1320 arranged in the pixel unit 1321 is shown. Each of the analog/digital conversion circuits 13230 outputs a pixel signal of a digital value obtained by performing analog/ digital conversion on a voltage value of an analog pixel signal input from the pixel 1320 of the corresponding column. In accordance with control from the horizontal scanning circuit 13222 within the reading unit 1322, the analog/digital conversion unit 1323 outputs the pixel signal of the digital value obtained by each of the analog/digital conversion circuits 13230 performing analog/digital conversion to the serializer 1324 via the horizontal signal line 1326.

Also, in FIG. 3, the analog/digital conversion unit 1323 having a configuration in which one analog/digital conversion circuit 13230 is provided for each column of the pixels 1320 within the pixel unit 1321, i.e., in one column, is shown. However, the configuration within the analog/digital conversion unit 1323 is not limited to the configuration shown in FIG. 3. For example, the analog/digital conversion unit 1323 may be configured to include one analog/digital conversion circuit 13230 with respect to a plurality of columns of the pixels 1320 within the pixel unit 1321. Also, one analog/digital conversion circuit 13230 may be configured to sequentially convert voltage values of analog pixel signals output from the pixels 1320 of each column according to analog/digital conversion.

The serializer 1324 performs parallel/serial conversion on pixel signals (digital values) sequentially input from the analog/digital conversion unit 1323, i.e., parallel RAW data. The serializer 1324 outputs the serial RAW data subjected to the parallel/serial conversion as an imaging signal (a visible-image capturing signal) to the outside of the visible-image capturing image sensor. At this time, the serializer 1324 outputs the serial RAW data as the visible-image capturing signal to the outside of the visible-image capturing image sensor, for example, in correspondence with a low voltage differential signaling (LVDS) scheme which is a differential interface scheme. In this case, the serializer 1324 also performs a process of terminating the LVDS scheme and the like.

Also, as described above, a plurality of pixels 1320 arranged in the pixel unit 1321 in the visible-image capturing image sensor are R, G, and B pixels. Also, in the fluorescence-image capturing image sensor, all the pixels 1320 arranged in the pixel unit 1321 are fluorescent pixels.

Also, the arrangements of the pixels 1320 in the visible-image capturing image sensor and the fluorescence-image capturing image sensor are not limited to the same arrangement. In other words, the total number of R, (and B pixels in the visible-image capturing image sensor and the number of fluorescent pixels in the fluorescence-image capturing image sensor are not limited to the same numbers of pixels. For example, the fluorescence-image capturing image sensor may have a smaller number of pixels than the visible-image capturing image sensor. In this case, for example, a region of one pixel 1320 (one fluorescent pixel) arranged in the fluorescence-image capturing image sensor may be a region for four pixels of the pixels 1320 arranged in the visible-image capturing image sensor (for four pixels of two rows and two columns). Thereby, an opening area for receiving light in the fluorescent pixel arranged in the fluorescence-image capturing image sensor is four times an operation area of any one of the R, G, and B pixels arranged in the fluorescence-image capturing image sensor and the fluorescent pixel arranged in the fluorescence-image capturing image sensor can receive more light.

Figure 4:
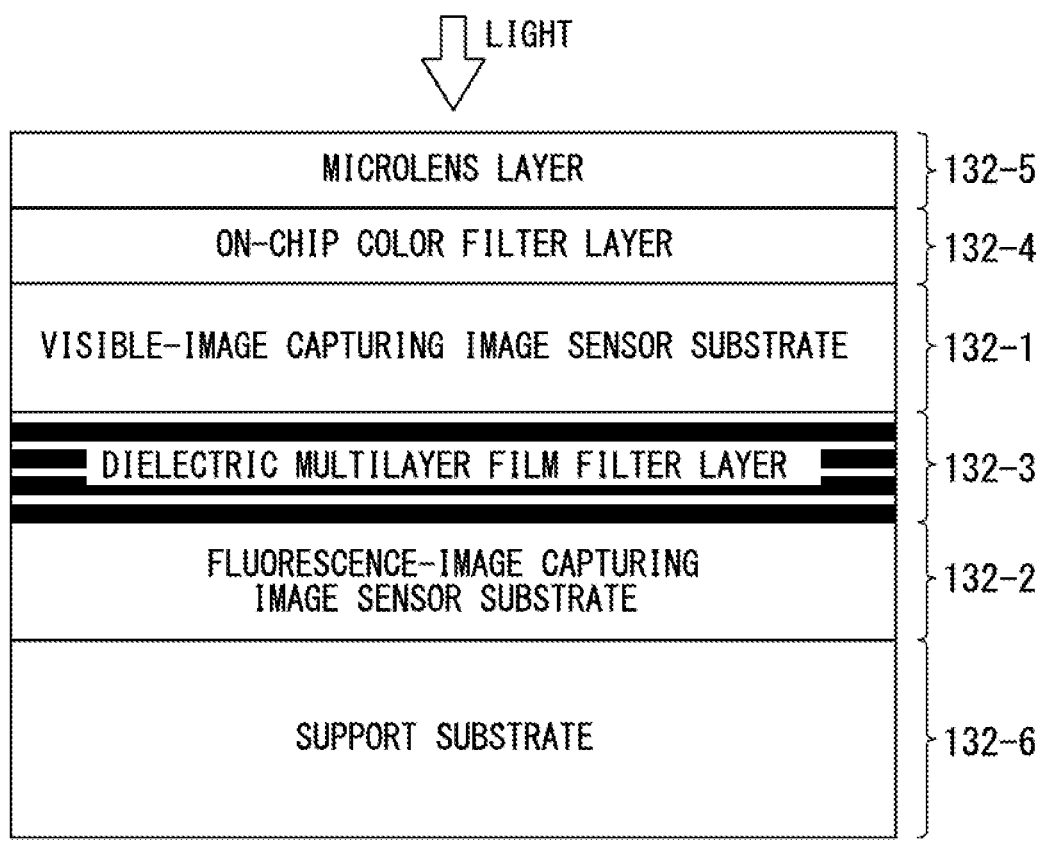
FIG. 4 is a cross-sectional view showing a schematic structure of the solid-state imaging device provided in the fluorescence observation endoscope device according to the embodiment of the present invention.

Subsequently, a schematic structure of the laminated image sensor 132 constituting the fluorescence observation device of the present invention in the fluorescence observation endoscope device 1 will be described. FIG. 4 is a cross-sectional view showing a schematic structure of the solid-state imaging device (the laminated image sensor 132) provided in the fluorescence observation endoscope device 1 according to the embodiment of the present invention. In FIG. 4, the overall longitudinal structure of the laminated image sensor 132 is schematically shown.

As described above, the laminated image sensor 132 has a structure in which a visible-image capturing image sensor and a fluorescence-image capturing image sensor are laminated with an interlayer filter interposed therebetween. More specifically, the laminated image sensor 132 is a structure in which a microlens layer 132-5, an on-chip color filter layer 132-4, a visible-image capturing image sensor substrate 132-1, a dielectric multilayer film filter layer 132-3, a fluorescence-image capturing image sensor substrate 132-2, and a support substrate 132-6 are laminated in this order in the direction of light propagation from the light incident side.

The microlens layer 132-5 is a layer in which a microlens is formed to concentrate incident light, i.e., reflected light (visible light) and fluorescence from the object 901 obtained by cutting the excitation light emitted from the excitation light cut filter 131, on each pixel arranged on the visible-image capturing image sensor substrate 132-1 and the fluorescence-image capturing image sensor substrate 132-2. In the microlens layer 132-5, microlenses are formed at positions corresponding to pixels arranged on the visible-image capturing image sensor substrate 132-1 and the fluorescence-image capturing image sensor substrate 132-2.

The on-chip color filter layer 132-4 is a layer on which an on-chip color filter is formed to transmit light of a predetermined wavelength band and cause the transmitted light to be incident on each pixel arranged on the visible-image capturing image sensor substrate 132-1. In the on-chip color filter layer 132-4, any one on-chip color filter for transmitting light of a wavelength band of red (R), green (G), or blue (B) (visible light) is formed at a position corresponding to each pixel arranged on the visible-image capturing image sensor substrate 132-1.

Also, in FIG. 4, the microlens layer 132-5 and the on-chip color filter layer 132-4 are formed on the entire surface of a side where light is incident on the laminated image sensor 132. However, in the laminated image sensor 132, each of the microlens layer 132-5 and the on-chip color filter layer 132-4 may be formed only in a pixel region arranged on the visible-image capturing image sensor substrate 132-1.

The visible-image capturing image sensor substrate 132-1 is a semiconductor substrate on which circuit elements for implementing a function of a visible-image capturing image sensor configured to output an imaging signal obtained by mainly allowing exposure with reflected light (visible light) are formed.

The dielectric multilayer film filter layer 132-3 is a layer on which a dielectric multilayer film filter which is an optical filter obtained by laminating inorganic materials such as dielectrics on multiple layers is formed to attenuate visible light incident on each pixel arranged on the fluorescence-image capturing image sensor substrate 132-2 by transmitting the visible light through the visible-image capturing image sensor substrate 132-1. The dielectric multilayer film filter is formed as an interlayer filter arranged between the visible-image capturing image sensor substrate 132-1 and the fluorescence-image capturing image sensor substrate 132-2. For example, the dielectric multilayer film filter is formed by alternately laminating a thin-film layer of 200 nm or less (for example, 100 nm) made of silicon dioxide ($SiO_2$) and a thin-film layer of 200 nm or less (for example, 50 nm) made of titanium oxide ($TiO_2$).

In the dielectric multilayer film filter, it is possible to increase an attenuation rate (a light shielding rate) of visible light by increasing the number of laminated thin-film layers, i.e., by increasing the thickness of the dielectric multilayer film filter. However, it is preferable to minimize the thickness of the dielectric multilayer film filter, i.e., the thickness of the dielectric multilayer film filter layer 132-3, to within 5 μm. Also, it is preferable that the number of thin-film layers of silicon dioxide ($SiO_2$) and titanium oxide ($TiO_2$) laminated when the dielectric multilayer film filter is formed be 50 or less (for example, 35). Thereby, in the laminated image sensor 132, it is possible to minimize significant deterioration in sensitivity to incoming light or oblique incidence characteristics for light incident in an oblique direction in each pixel arranged on the fluorescence-image capturing image sensor substrate 132-2 without excessively increasing the distance from the microlens layer 132-5 to the fluorescence-image capturing image sensor substrate 132-2. Also, the thickness of the dielectric multilayer film filter layer 132-3 described above does not become a thickness in which a dielectric multilayer film filter having a high attenuation rate is formed to attenuate visible light incident on each pixel arranged on the fluorescence-image capturing image sensor substrate 132-2 to a negligible level.

The fluorescence-image capturing image sensor substrate 132-2 is a semiconductor substrate on which each circuit element is formed to implement a function of the fluorescence-image capturing image sensor which outputs an imaging signal obtained by mainly allowing exposure with the fluorescence transmitted through the visible-image capturing image sensor substrate 132-1.

The support substrate 132-6 is a semiconductor substrate for strongly supporting the whole of the laminated image sensor 132 in which the microlens layer 132-5, the on-chip color filter layer 132-4, the visible-image capturing image sensor substrate 132-1, the dielectric multilayer film filter layer 132-3, and the fluorescence-image capturing image sensor substrate 132-2 are laminated.

Figure 5:
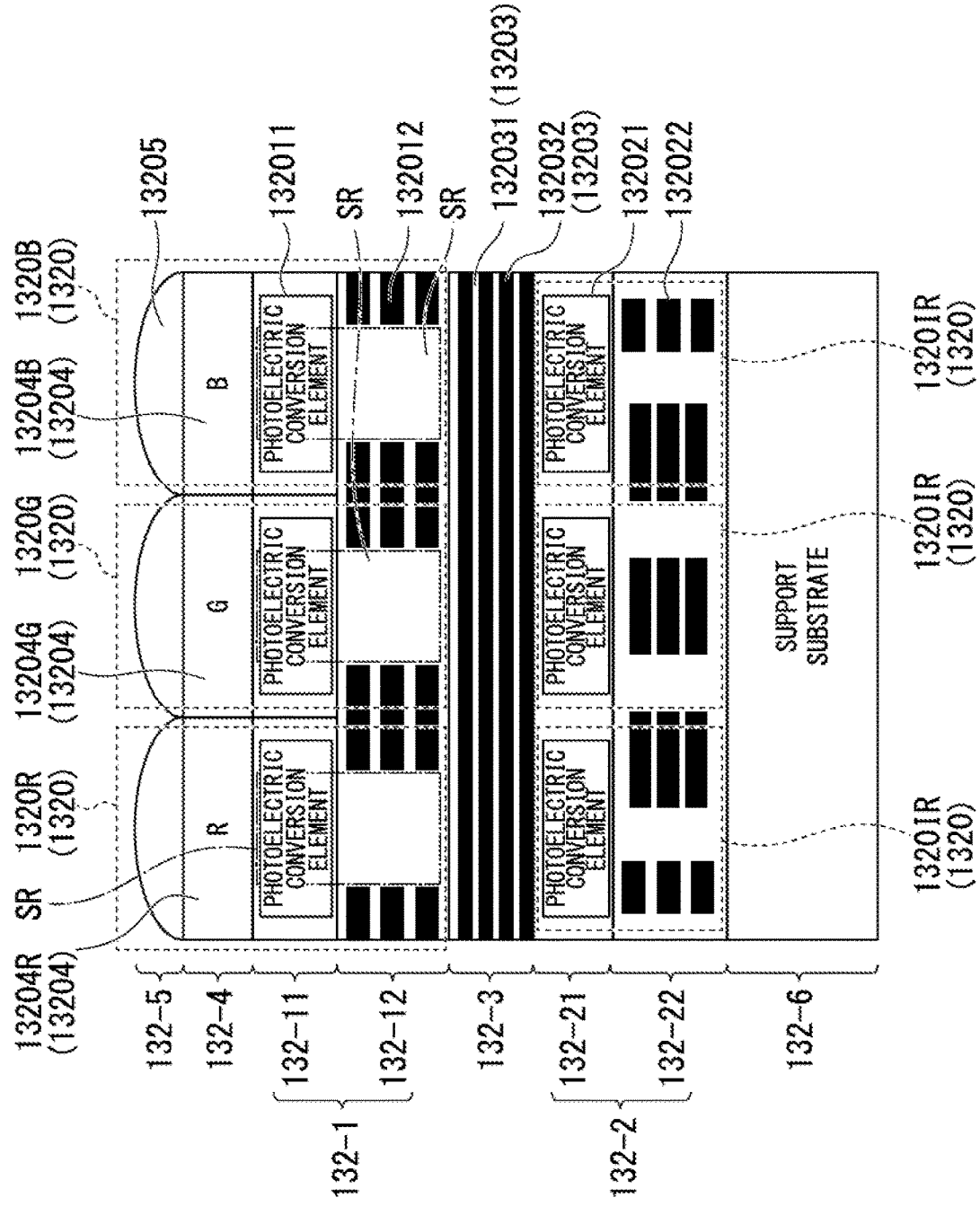
FIG. 5 is a cross-sectional view showing an example of a structure of the solid-state imaging device provided in the fluorescence observation endoscope device according to the embodiment of the present invention.

Next, a more detailed structure of the laminated image sensor 132 constituting the fluorescence observation device of the present invention in the fluorescence observation endoscope device 1 will be described. FIG. 5 is a cross-sectional view showing an example of a structure of the solid-state imaging device (the laminated image sensor 132) provided in the fluorescence observation endoscope device 1 according to the embodiment of the present invention. In FIG. 5, a longitudinal structure of a region where R, G, and B pixels are formed in the visible-image capturing image sensor, i.e., a part of the pixel unit 1321, in the laminated image sensor 132 is schematically shown. Also, in FIG. 5, a case in which fluorescent pixels are formed, i.e., three fluorescent pixels are formed, at positions corresponding to the R, G, and B pixels formed in the visible-image capturing image sensor in the fluorescence-image capturing image sensor constituting the laminated image sensor 132 is shown.

As described above, the laminated image sensor 132 is formed by laminating each layer constituting the pixel 1320 and the image sensor substrate (the fluorescence-image capturing image sensor substrate 132-2 and the visible-image capturing image sensor substrate 132-1) on the support substrate 132-6. Also, each of the fluorescence-image capturing image sensor substrate 132-2 and the visible-image capturing image sensor substrate 132-1 is formed by a photoelectric conversion layer and a wiring layer. More specifically, the fluorescence-image capturing image sensor substrate 132-2 is formed by the photoelectric conversion layer 132-21 and the wiring layer 132-22. Also, the visible-image capturing image sensor substrate 132-1 is formed by the photoelectric conversion layer 132-11 and the wiring layer 132-12. Each of the fluorescence-image capturing image sensor substrate 132-2 and the visible-image capturing image sensor substrate 132-1 is a backside illumination (BSI) type solid-state imaging device. Accordingly, the laminated image sensor 132 has a configuration in which the wiring layer 132-22, the photoelectric conversion layer 132-21, the dielectric multilayer film filter layer 132-3, the wiring layer 132-12, the photoelectric conversion layer 132-11, the on-chip color filter layer 132-4, and the microlens layer 132-5 are laminated in this order on the support substrate 132-6 toward a side where light is incident.

The wiring layer 132-22 is a layer for forming wiring in each circuit element which implements the function of the fluorescence-image capturing image sensor. In FIG. 5, a state in which wiring 132022 for connecting circuit elements of a fluorescent pixel (hereinafter referred to as a "fluorescent pixel 1320IR") which is each pixel 1320 arranged on the fluorescence-image capturing image sensor substrate 132-2 is formed on the wiring layer 132-22 is schematically shown. Each fluorescent pixel 1320IR outputs a pixel signal (an analog signal) according to the driving signal from the vertical scanning circuit 13221 input through the wiring 132022 formed in the wiring layer 132-22 to the vertical signal line 1325 through the wiring 132022.

The photoelectric conversion layer 132-21 is a layer for forming a photoelectric conversion element constituting the fluorescent pixel 1320IR. In FIG. 5, a state in which a photoelectric conversion element 132021 constituting each of the three fluorescent pixels 1320IR is formed on the photoelectric conversion layer 132-21 is schematically shown. Each photoelectric conversion element 132021 generates and stores signal charges according to an intensity of incident light. More specifically, each photoelectric conversion element 132021 generates and stores signal charges according to intensities of reflected light (visible light) and fluorescence incident from the microlens layer 132-5 to the visible-image capturing image sensor substrate 132-1 via the on-chip color filter layer 132-4 and transmitted through an opening of the corresponding pixel 1320 (a substrate region SR shown in FIG. 5) formed on the visible-image capturing image sensor substrate 132-1 and the dielectric multilayer film filter layer 132-3.

As described above, for example, the dielectric multilayer film filter 13203 is formed on the dielectric multilayer film filter layer 132-3 by alternately laminating a thin-film layer of silicon dioxide ($SiO_2$) and a thin-film layer of titanium oxide ($TiO_2$). The dielectric multilayer film filter 13203 causes only light of a visible-light wavelength band within reflected light (visible light) and fluorescence transmitted through the substrate region SR of the opening of the pixel 1320 formed on the visible-image capturing image sensor substrate 132-1 to be reflected or absorbed and attenuated and causes light of a wavelength band of the fluorescence to be transmitted. In FIG. 5, a state in which four silicon dioxide ($SiO_2$) thin-film layers 132031 and four titanium oxide ($TiO_2$) thin-film layers 132032 are alternately laminated to form the dielectric multilayer film filter 13203 is schematically shown.

The wiring layer 132-12 is a layer for forming wiring in each circuit element which implements the function of the visible-image capturing image sensor. In FIG. 5, a state in which wiring 132012 for connecting circuit elements of each pixel 1320 arranged in the visible-image capturing image sensor is formed on the wiring layer 132-12 is schematically shown. Also, in the following description, an R pixel which is a pixel 1320 arranged in the visible-image capturing image sensor is referred to as an "R pixel 1320R", a G pixel is referred to as a "G pixel 1320G", and a B pixel is referred to as a "B pixel 1320B". Each of the R pixel 1320R, the G pixel 1320G, and the B pixel 1320B outputs a pixel signal (an analog signal) according to a driving signal from the vertical scanning circuit 13221 input through the wiring 132012 formed in the wiring layer 132-12 to the vertical signal line 1325 through the wiring 132012.

The photoelectric conversion layer 132-11 is a layer for forming a photoelectric conversion element constituting each of the R pixel 1320R, the G pixel 1320G, and the B pixel 1320B. In FIG. 5, a state in which the photoelectric conversion element 132011 constituting each of the R pixel 1320R, the G pixel 1320G, and the B pixel 1320B is formed on the photoelectric conversion layer 132-11 is schematically shown. Each photoelectric conversion element 132011 generates and stores signal charges according to the intensity of incident light. More specifically, each photoelectric conversion element 132011 generates and stores signal charges according to the intensity of reflected light (visible light) incident from the microlens layer 132-5 via the on-chip color filter layer 132-4.

Also, the visible-image capturing image sensor substrate 132-1 transmits a part of light of a visible-light wavelength band and light of a fluorescence wavelength band which have not been used in generation of signal charges by the photoelectric conversion element 132011 formed on the photoelectric conversion layer 132-11 within reflected light (visible light) and fluorescence which have been incident. In other words, the visible-image capturing image sensor substrate 132-1 also functions as an optical filter configured to absorb and attenuate light of the visible-light wavelength band used in the generation of the signal charges by the photoelectric conversion element 132011 within the reflected light (the visible light) and the fluorescence which have been incident.

The on-chip color filter layer 132-4 causes visible light in any one of the red (R), green (G), and blue (B) wavelength bands to be transmitted through the formed on-chip color filter 13204 and causes the transmitted visible light to be incident on the photoelectric conversion element 132011 formed on the photoelectric conversion layer 132-11. Also, the on-chip color filter 13204 also causes light of an infra-red-light wavelength band, i.e., light of a fluorescence wavelength band, to be transmitted in addition to visible light of a corresponding wavelength band. In FIG. 5, a state in which an on-chip color filter 13204R for causing visible light of the red (R) wavelength band to be transmitted is formed at a position corresponding to the R pixel 1320R, an on-chip color filter 13204G for causing visible light of the green (G) wavelength band to be transmitted is formed at a position corresponding to the G pixel 1320G and an on-chip color filter 13204B for causing visible light of the blue (B) wavelength band to be transmitted is formed at a position corresponding to the B pixel 1320B is schematically shown. Also, in the laminated image sensor 132, the on-chip color filter 13204R, the on-chip color filter 13204G; and the on-chip color filter 13204B are formed in, for example, a Bayer array.

The microlens layer 132-5 causes reflected light (visible light) and fluorescence incident on the laminated image sensor 132 to be concentrated on each of the photoelectric conversion elements 132011 formed in the photoelectric conversion layer 132-11 by the formed microlens 13205. In FIG. 5, a state in which microlenses 13205 corresponding to three photoelectric conversion elements 132011 formed on the photoelectric conversion layer 132-11 are formed is schematically shown.

Figure 6:
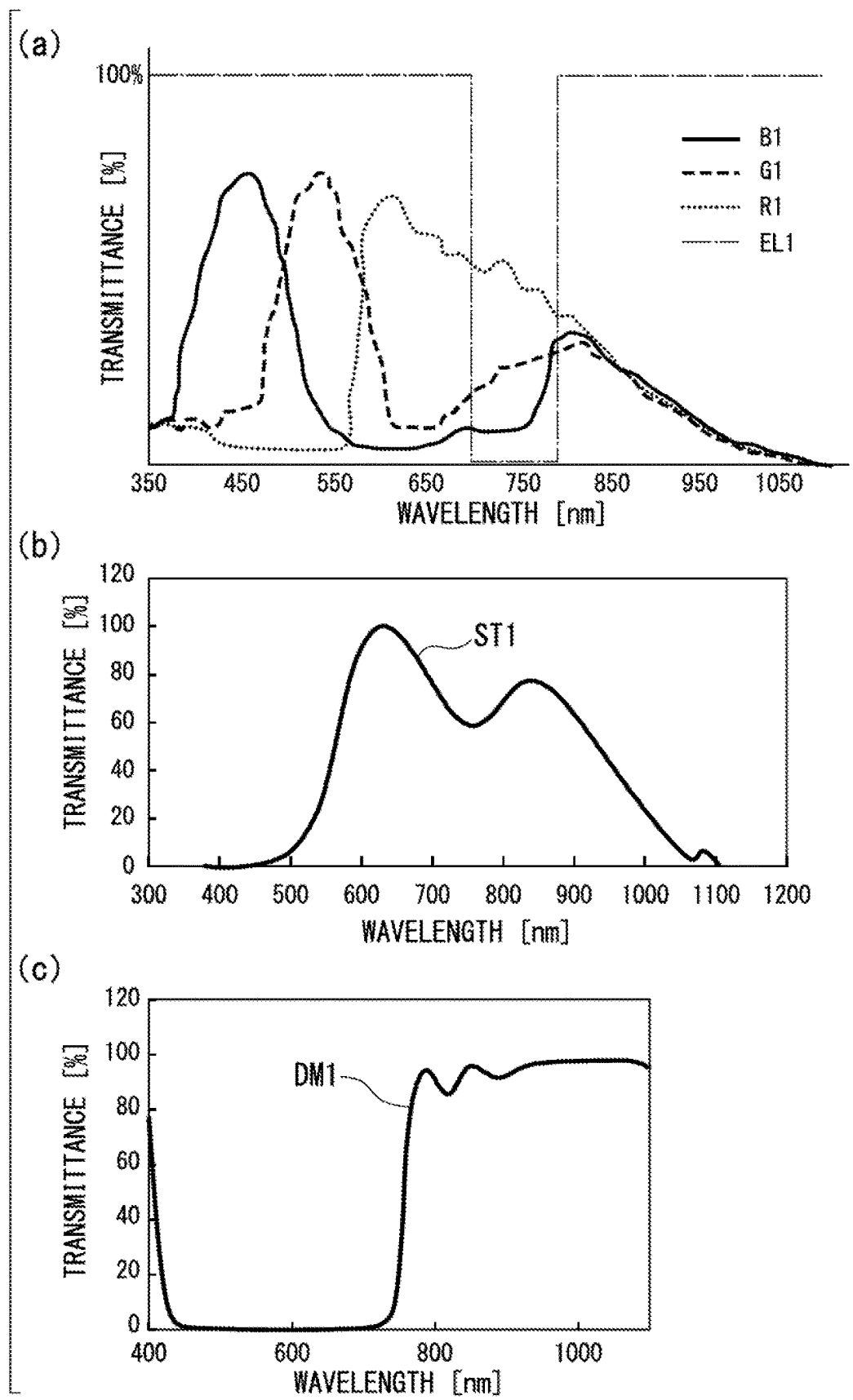
FIG. 6 is a diagram showing an example of characteristics of filters corresponding to pixels of the solid-state imaging device provided in the fluorescence observation endoscope device according to the embodiment of the present invention.

Next, characteristics of the laminated image sensor 132 with respect to the wavelength band of light incident on each pixel 1320 will be described. FIG. 6 is a diagram showing an example of characteristics of filters corresponding to the pixels 1320 of the solid-state imaging device (the laminated image sensor 132) provided in the fluorescence observation endoscope device 1 according to the embodiment of the present invention. In (a) of FIG. 6, an example of characteristics of filters corresponding to the pixels 1320 arranged on the visible-image capturing image sensor substrate 132-1 constituting the laminated image sensor 132 is shown. Also, in (b) of FIG. 6, an example of characteristics of light transmitted through the visible-image capturing image sensor substrate 132-1 constituting the laminated image sensor 132 is shown. Also, in (c) of FIG. 6, an example of characteristics of the dielectric multilayer film filter 13203 constituting the laminated image sensor 132 is shown.

In (a) of FIG. 6 to (c) of FIG. 6, the horizontal axis represents a light wavelength and the vertical axis represents light transmittance characteristics (hereinafter referred to as "spectroscopic characteristics"). More specifically, in (a) of FIG. 6, B1 represents spectroscopic characteristics of the on-chip color filter 13204B, G1 represents spectroscopic characteristics of the on-chip color filter 13204G, and R1 represents spectroscopic characteristics of the on-chip color filter 13204R. In (b) of FIG. 6, ST1 represents spectroscopic characteristics in which a ratio of light transmitted through the visible-image capturing image sensor substrate 132-1 (light transmitted through the substrate region SR of the opening of the pixel 1320 shown in FIG. 5) to a maximum value is represented as transmittance in a case in which the visible-image capturing image sensor substrate 132-1 is regarded to be an optical filter. Also, in (c) of FIG. 6, DM1 represents spectroscopic characteristics of the dielectric multilayer film filter 13203. Also, in (a) of FIG. 6, spectroscopic characteristics EL1 of the excitation light cut filter 131 configured to attenuate or cut light of an excitation-light wavelength band incident on the laminated image sensor 132 are also shown.

As shown in (a) of FIG. 6, the spectroscopic characteristics B1 of the on-chip color filter 13204B corresponding to the B pixel 1320B are characteristics having high transmittance with respect to light of a wavelength band of 400 nm to 500 nm which is the blue (B) wavelength band. Accordingly, the on-chip color filter 13204B selects (transmits) the visible light of the blue (B) wavelength band of 400 nm to 500 nm and causes the selected (transmitted) visible light to be incident on the photoelectric conversion element 132011 of the B pixel 1320B.

Also, as shown in (a) of FIG. 6, the spectroscopic characteristics G1 of the on-chip color filter 13204G corresponding to the G pixel 1320G are characteristics having high transmittance with respect to light of a wavelength band of 500 nm to 600 nm which is the green (G) wavelength band. Accordingly, the on-chip color filter 13204G selects (transmits) the visible light of the green (G) wavelength band of 500 nm to 600 nm and causes the selected (transmitted) visible light to be incident on the photoelectric conversion element 132011 of the G pixel 1320G.

Also, as shown in (a) of FIG. 6, the spectroscopic characteristics R1 of the on-chip color filter 13204R corresponding to the R pixel 1320R are characteristics having high transmittance with respect to light of a wavelength band of 600 nm to 700 nm which is the red (R) wavelength band.

Accordingly, the on-chip color filter 13204R selects (transmits) the visible light of the red (R) wavelength band of 600 nm to 700 nm and causes the selected (transmitted) visible light to be incident on the photoelectric conversion element 132011 of the R pixel 1320R.

Also, because the on-chip color filter 13204 is formed of an organic material, the on-chip color filter 13204 also causes visible light of a wavelength band which is not a selected wavelength band, i.e., which is not an intended wavelength band, to be transmitted, as shown in (a) of FIG. 6. Thus, light other than light of a wavelength band to be used for exposure (detected) is also incident on the photoelectric conversion element 132011 of each pixel 1320. More specifically, near-infrared light in a wavelength band exceeding 800 nm, i.e., fluorescence, is also incident on each photoelectric conversion element 132011, as shown in (a) of FIG. 6.

However, in the fluorescence observation endoscope device 1, the fluorescence is significantly weak light excited by the excitation light of ICG administered to the person to be examined (subjected to fluorescence emission). Thus, the fluorescence incident on the photoelectric conversion element 132011 of each of the R pixel 1320R, the G pixel 1320G, and the B pixel 1320B arranged on the visible-image capturing image sensor substrate 132-1 has a level which is negligible with respect to the visible light of the wavelength band to be selected (transmitted) by the on-chip color filter 13204. Accordingly, the photoelectric conversion element 132011 of each of the R pixel 1320R, the G pixel 1320G, and the B pixel 1320B arranged on the visible-image capturing image sensor substrate 132-1 in the laminated image sensor 132 generates and stores signal charges according to an intensity of visible light which has been transmitted through the corresponding on-chip color filters 13204 and has been incident. Thereby, the visible-image capturing image sensor outputs a visible-image capturing signal obtained by allowing exposure with visible light.

Also, the visible-image capturing image sensor substrate 132-1 transmits a part of visible light and fluorescence which have not been used in generation of signal charges by the photoelectric conversion elements 132011 as described above. More specifically, a part of visible light and fluorescence is transmitted from the substrate region SR of the opening of the pixel 1320 shown in FIG. 5. In (b) of FIG. 6, spectroscopic characteristics of light transmitted through the substrate region SR of the opening of the pixel 1320 by the visible-image capturing image sensor substrate 132-1 are shown. The spectroscopic characteristics ST1 shown in (b) of FIG. 6 are represented by a ratio of a wavelength-band-specific sensitivity to light in the photoelectric conversion element 132021 of the fluorescent pixel 1320IR arranged on the fluorescence-image capturing image sensor substrate 132-2 measured in a configuration in which no dielectric multilayer film filter layer 132-3 is laminated in the laminated image sensor 132, i.e., a result of measuring a spectroscopic sensitivity, to a maximum value. The spectroscopic characteristics ST1 correspond to an intensity of light incident on the fluorescence-image capturing image sensor substrate 132-2 without involving the dielectric multilayer film filter layer 132-3 represented for each wavelength band and represent spectroscopic characteristics of the visible-image capturing image sensor substrate 132-1 when the visible-image capturing image sensor substrate 132-1 is regarded to be an optical filter.

As shown in (b) of FIG. 6, the spectroscopic characteristics ST1 of the visible-image capturing image sensor substrate 132-1 are characteristics having high transmittance with respect to light of a wavelength band (500 nm to 1100 nm) of near-infrared light from a part of visible light. Accordingly, the visible-image capturing image sensor substrate 132-1 transmits light of the wavelength band exceeding 500 nm and emits the transmitted light to the dielectric multilayer film filter 13203. In other words, the visible-image capturing image sensor substrate 132-1 causes light of the wavelength band of 500 nm or less to be attenuated.

The dielectric multilayer film filter 13203 causes light of a wavelength band of 450 nm to 750 nm to be attenuated as shown in the spectroscopic characteristics DM1 shown in (c) of FIG. 6. Accordingly, the dielectric multilayer film filter 13203 transmits near-infrared light (fluorescence) of a wavelength band exceeding 750 nm within light of the wavelength band of 500 nm to 1100 nm incident from the visible-image capturing image sensor substrate 132-1 and causes the transmitted near-infrared light (fluorescence) to be incident on the photoelectric conversion element 132021 of each fluorescent pixel 1320IR arranged on the fluorescence-image capturing image sensor substrate 132-2.

Figure 7:
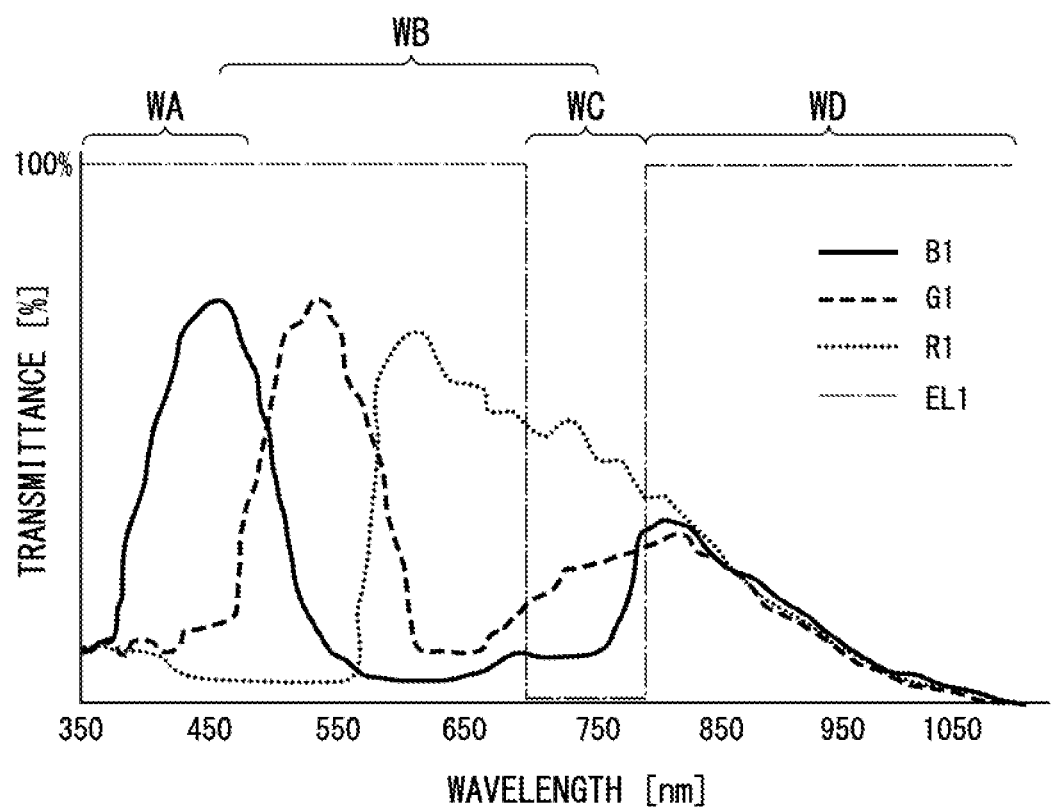
FIG. 7 is a diagram showing an example of characteristics of light incident on a fluorescence-image capturing image sensor constituting the solid-state imaging device provided in the fluorescence observation endoscope device according to the embodiment of the present invention.

Here, the wavelength band of light incident on each fluorescent pixel 1320IR arranged on the fluorescence-image capturing image sensor substrate 132-2 will be described. FIG. 7 is a diagram showing an example of characteristics of light incident on the fluorescence-image capturing image sensor (the fluorescence-image capturing image sensor substrate 132-2) constituting the solid-state imaging device (the laminated image sensor 132) provided in the fluorescence observation endoscope device 1 according to the embodiment of the present invention. In FIG. 7, a wavelength band range based on characteristics of light transmitted through the visible-image capturing image sensor substrate 132-1 shown in (b) of FIG. 6 and characteristics of the dielectric multilayer film filter 13203 shown in (c) of FIG. 6 in an example of characteristics of each filter corresponding to the pixel 1320 arranged on the visible-image capturing image sensor substrate 132-1 shown in (a) of FIG. 6 is shown.

Reflected light (visible light) and fluorescent light obtained by reflecting or absorbing and attenuating light of a wavelength band WC (light of the excitation-light wavelength band) in the excitation light cut filter 131 are incident on the laminated image sensor 132 (see spectroscopic characteristics EL1). In the laminated image sensor 132, the visible light of the wavelength band WA within the incident reflected light (visible light) and fluorescence is absorbed and attenuated by the visible-image capturing image sensor substrate 132-1 (see the spectroscopic characteristics ST1 shown in (b) of FIG. 6). Also, in the laminated image sensor 132, visible light of the wavelength band WB within the incident reflected light (visible light) and fluorescence is attenuated by the dielectric multilayer film filter 13203 (see the spectroscopic characteristics DM1 shown in (c) of FIG. 6). Thus, only the fluorescence (near-infrared light) of the wavelength band WD is incident on the photoelectric conversion element 132021 of each fluorescent pixel 1320IR arranged on the fluorescence-image capturing image sensor substrate 132-2 in the laminated image sensor 132. Then, the photoelectric conversion element 132021 generates and stores signal charges according to an intensity of incident fluorescence of the wavelength band WD. Thereby, the fluorescence-image capturing image sensor outputs a fluorescence-image capturing signal obtained by allowing exposure with only the fluorescence.

However, this is a case in which the visible-image capturing image sensor substrate 132-1 has attenuated or removed (cut) all the visible light of the wavelength band WA and the dielectric multilayer film filter 13203 has attenuated or removed (cut) all the visible light of the wavelength band WB. Here, in order to attenuate or remove (cut) all the visible light of the wavelength band WA and the wavelength band WB, it is necessary to significantly increase attenuation rates (light shielding rates) of the visible-image capturing image sensor substrate 132-1 and the dielectric multilayer film filter 13203.

As described above, it is possible to increase the attenuation rate by increasing the numbers of silicon dioxide ($SiO_2$) thin-film layers 132031 and titanium oxide ($TiO_2$) thin-film layers 132032 alternately laminated to form the dielectric multilayer film filter 13203 and increasing a thickness in the dielectric multilayer film filter 13203. Likewise, in the visible-image capturing image sensor substrate 132-1, it is also possible to increase the attenuation rate by increasing a thickness of the photoelectric conversion layer 132-11 formed on the visible-image capturing image sensor substrate 132-1. However, when the thickness of the photoelectric conversion layer 132-11 is increased, the photoelectric conversion layer 132-11 may absorb and attenuate fluorescence to be detected by the fluorescence-image capturing image sensor substrate 132-2 as well as the visible light. From this fact, increasing the attenuation rate of the visible light of the wavelength band WA by increasing the thickness of the visible-image capturing image sensor substrate 132-1 is considered to be less effective. If the attenuation rate (the light shielding rate) of the wavelength band of 450 nm or less is increased, extending the visible light range of the wavelength band WB which is attenuated by the dielectric multilayer film filter 13203 to a range of a wavelength band of 450 nm or less, more specifically, extending the visible light range of the wavelength band WB which is attenuated by the dielectric multilayer film filter 13203 to the visible light range of the wavelength band WA which is attenuated by the visible-image capturing image sensor substrate 132-1, is considered to be effective.

However, as shown in FIG. 4 and FIG. 5, the laminated image sensor 132 is a structure in which the fluorescence-image capturing image sensor substrate 132-2 is laminated on a surface opposite a surface of a side where light is incident on the visible-image capturing image sensor substrate 132-1. Thus, in the laminated image sensor 132, it is difficult to increase the light shielding rate in the visible-image capturing image sensor substrate 132-1 or the dielectric multilayer film filter 13203 to a light shielding rate for attenuating or removing (cutting) all visible light of the wavelength band WA and the wavelength band WB. That is, in the laminated image sensor 132, it is difficult to increase the thickness of the visible-image capturing image sensor substrate 132-1 or the dielectric multilayer film filter 13203 in order to increase the light shielding rate.

This is because the distance between the photoelectric conversion element 132021 of each fluorescent pixel 1320IR arranged on the fluorescence-image capturing image sensor substrate 132-2 and the corresponding microlens 13205 is lengthened and the sensitivity and oblique incidence characteristics for light in each photoelectric conversion element 132021 are deteriorated when the thickness of the visible-image capturing image sensor substrate 132-1 or the dielectric multilayer film filter 13203 is increased to increase the light shielding rate.

Thus, in the laminated image sensor 132, the thicknesses of the visible-image capturing image sensor substrate 132-1 or the dielectric multilayer film filter 13203 does not have a thickness for an increase to a light shielding rate for attenuating or removing (cutting) all visible light of the wavelength band WA and the wavelength band WB. That is, in the laminated image sensor 132, the deterioration of the sensitivity and the oblique incidence characteristics for light in the photoelectric conversion element 132021 of each fluorescent pixel 1320IR arranged on the fluorescence-image capturing image sensor substrate 132-2 is minimized. Accordingly, in the laminated image sensor 132, a small amount of visible light is also incident on the photoelectric conversion element 132021.

Also, as described above, in the fluorescence observation endoscope device 1, the excitation light cut filter 131 arranged outside the laminated image sensor 132 causes reflected light and fluorescence from the object 901 to be incident on the laminated image sensor 132 by removing (cutting) substantially all excitation light of the wavelength band WC as in the spectroscopic characteristics EL1 shown in (a) of FIG. 6. Thus, the excitation light cut filter 131 is significantly thick to significantly increase the attenuation rate (the light shielding rate) with respect to the excitation light of the wavelength band (the wavelength band of 700 nm to 800 nm) in the wavelength band WC. For example, the excitation light cut filter 131 is also formed by laminating a plurality of thin-film layers as in the dielectric multilayer film filter 13203. However, in the excitation light cut filter 131, the attenuation rate (the light shielding rate) for the excitation light of the wavelength band WC is significantly increased by forming a larger number of thin-film layers (for example, 100 layers) than in the dielectric multilayer film filter 13203. This is because the excitation light cut filter 131 is arranged outside the laminated image sensor 132 and therefore there is no influence on the sensitivity and the oblique incidence characteristics for light in the photoelectric conversion element 132021 of each fluorescent pixel 1320IR arranged on the fluorescence-image capturing image sensor substrate 132-2 constituting the laminated image sensor 132.

Meanwhile, as described above, the fluorescence to be used for exposure (detected) by the photoelectric conversion element 132021 of each fluorescent pixel 1320IR arranged on the fluorescence-image capturing image sensor substrate 132-2 is significantly weak light capable of being ignored with respect to visible light. Thus, when the light shielding rates of the visible light of the wavelength band WA and the wavelength band WB incident on each photoelectric conversion element 132021 are low, it becomes difficult to ignore levels of the wavelength band WA and the wavelength band WB which are not wavelength bands to be used for exposure (detected) by the photoelectric conversion element 132021. Then, the exposure (detection) accuracy of fluorescence of the wavelength band WD in the photoelectric conversion element 132021 deteriorates.

Therefore, in the present invention, the setting unit 21 provided in the light source device 20 controls an intensity of white light emitted by the white light source 221, i.e., an intensity of visible light separated by the dichroic mirror 231. Thereby, in the present invention, an intensity of visible light incident on the fluorescence-image capturing image sensor substrate 132-2 has an appropriate level or less at which the exposure (detection) accuracy of fluorescence in the photoelectric conversion element of each fluorescent pixel 1320IR does not deteriorate in a state in which reflected light (visible light) from the object 901 to which illumination light emitted by the light source device 20 is radiated is not attenuated.

More specifically, the setting unit 21 monitors a digital value indicating a magnitude of a monitoring signal for setting an intensity of white light output from the image processing unit 32 provided in the external processing unit 30, i.e., a pixel signal output by each pixel 1320 arranged on the visible-image capturing image sensor substrate 132-1 included in the parallel RAW data (hereinafter referred to as a "visible-light signal intensity"). Then, the setting unit 21 determines each monitored visible-light signal intensity on the basis of the presetting signal intensity (hereinafter referred to as a "setting signal intensity") and controls a light emission intensity of white light (visible light) due to the white light source 221 in accordance with the determination result. Here, the setting signal intensity is a maximum digital value or a fixed digital value preset with respect to the digital value of the pixel signal output by the pixel 1320.

When the setting signal intensity is the preset maximum digital value, the setting unit 21 determines whether or not the visible-light signal intensity of any monitored pixel 1320 exceeds the setting signal intensity. If the setting unit 21 determines that the visible-light signal intensity of any monitored pixel 1320 exceeds the setting signal intensity, the setting unit 21 controls the white light source 221 so that the light emission intensity is decreased. If the setting unit 21 determines that the visible-light signal intensity of any monitored pixel 1320 does not exceed the setting signal intensity, the white light source 221 is controlled so that the current emission intensity is maintained.

Thereby, the setting unit 21 can minimize digital values of pixel signals output by all the pixels 1320 arranged on the visible-image capturing image sensor substrate 132-1, i.e., magnitudes of pixel signals, to a preset maximum magnitude or less. Thereby, visible light incident without attenuation disappears on the fluorescence-image capturing image sensor substrate 132-2 and the exposure (detection) accuracy of fluorescence in the photoelectric conversion elements 132021 of all the arranged fluorescent pixels 1320IR does not deteriorate.

Also, if the setting signal intensity is a preset fixed digital value, the setting unit 21 determines whether or not the visible-light signal intensity of any monitored pixel 1320 is greater than the setting signal intensity. If the setting unit 21 determines that the visible-light signal intensity of any monitored pixel 1320 is greater than the setting signal intensity, the setting unit 21 controls the white light source 221 so that the light emission intensity is decreased. If the setting unit 21 determines that the visible-light signal intensity of any monitored pixel 1320 is less than the setting signal intensity, the setting unit 21 controls the white light source 221 so that the light emission intensity is increased. Also, if the setting signal intensity is a preset fixed digital value, it is not necessarily determined that the visible-light signal intensities of all monitored pixels 1320 are greater or less than the setting signal intensity. In other words, the visible-light signal intensity of the pixel 1320 determined to be greater than the setting signal intensity and the visible-light signal intensity of the pixel 1320 determined to be less than the setting signal intensity may be mixed among the visible-light signal intensities of the pixels 1320 monitored by the setting unit 21. In this case, the setting unit 21 controls the light emission intensity of the white light source 221, i.e., performs control for decreasing the light emission intensity, so that the visible-light signal intensity of the pixels 1320 determined to be greater than the setting signal intensity disappears, i.e., so that the visible light intensities of all the monitored pixels 1320 are less than or equal to the setting signal intensity.

Thereby, the setting unit 21 can minimize digital values of pixel signals (magnitudes of pixel signals) output by all pixels 1320 arranged on the visible-image capturing image sensor substrate 132-1 to within a preset fixed magnitude. Thereby, visible light incident without attenuation disappears on the fluorescence-image capturing image sensor substrate 132-2 and the exposure (detection) accuracy of fluorescence in the photoelectric conversion elements 132021 of all the arranged fluorescent pixels 1320IR does not deteriorate.

Also, the monitoring of the visible-light signal intensity of the pixel 1320 in the setting unit 21 may be performed for each monitoring signal (parallel RAW data) output from the image processing unit 32, i.e., for each frame in which the visible-image capturing image sensor allows exposure with reflected light (visible light) and photographs the object 901 or may be performed at preset frame intervals, for example, at a ratio of one monitoring operation during 10 frames. Also, the monitoring of the visible-light signal intensity of the pixel 1320 in the setting unit 21 may be performed in a frame cycle in which the visible-image capturing image sensor allows exposure with the reflected light (the visible light), i.e., at a timing synchronized with a frame rate or may be performed asynchronously with a frame rate. For example, in accordance with an instruction (an instruction signal) for monitoring the visible-light signal intensity and adjusting illumination light emitted by the light source device 20 input by the examiner operating the photographing control switch 14, the setting unit 21 may monitor the visible-light signal intensity of the pixel 1320 and control the light emission intensity of the white light source 221. Also, the range of the pixels 1320 in which the setting unit 21 monitors the visible-light signal intensity may be the whole of one frame or may be a predetermined range of one frame. For example, the range may be a range preset from the center of one frame, i.e., a range in which a so-called main object (the object 901) may be photographed. Thereby, the light emission intensity of the white light source 221 can be controlled at a higher speed.

Here, a method in which the fluorescence observation endoscope device 1 sets the setting signal intensity for controlling an intensity of illumination light emitted by the light source device 20 constituting the fluorescence observation device of the present invention (a light emission intensity of white light (visible light) emitted by the white light source 221) will be described. When the light emission intensity of the white light source 221 is controlled in accordance with predetermined conditions, the setting unit 21 sets the setting signal intensity by using the monitoring signal output from the image processing unit 32 provided in the external processing unit 30.

More specifically, the light emission intensity of the white light (visible light) emitted by the white light source 221 is gradually changed (for example, gradually increased from a low level to a high level at intervals of a predetermined emission intensity level) and the laminated image sensor 132 performs photographing in each light emission intensity. At this time, the white light source 222 does not emit white light which is separated to be excitation light by the dichroic mirror 232. The object photographed by the laminated image sensor 132 at this time is assumed to be a reference object (for example, a white object).

Then, the image processing unit 32 provided in the external processing unit 30 outputs the monitoring signal (parallel RAW data) in each light emission intensity to the setting unit 21 provided in the light source device 20. The setting unit 21 sets a setting signal intensity on the basis of a visible-light signal intensity indicated by parallel RAW data of a visible-image capturing signal output by the visible-image capturing image sensor and a signal intensity indicated by parallel RAW data of a fluorescence-image capturing signal output by the fluorescence-image capturing image sensor (hereinafter referred to as a "fluorescence signal intensity") included in each monitoring signal output from the image processing unit 32.

Also, for the visible-light signal intensity and the fluorescence signal intensity to be used when the setting unit 21 sets the setting signal intensity, the pixels 1320 arranged on the visible-image capturing image sensor substrate 132-1, i.e., the R pixel 1320R, the G pixel 1320G, and the B pixel 1320B, may be distinguished from each other or the pixels 1320 may not be distinguished from each other. If the setting unit 21 sets the setting signal intensity without distinguishing the pixels 1320, it is possible to facilitate the above-described process of monitoring the visible-light signal intensity of each pixel 1320 output by the visible-image capturing image sensor when the light emission intensity of the white light source 221 is controlled.

In the following description, a case in which the setting unit 21 sets the setting signal intensity by distinguishing the R pixel 1320R, the G pixel 1320G, and the B pixel 1320B will be described for more detailed description of a process in which the setting unit 21 sets the setting signal intensity. Also, when the setting unit 21 sets the setting signal intensity by distinguishing the R pixel 1320R, the G pixel 1320G, and the B pixel 1320B, it is possible to set the setting signal intensity for each pixel 1320 arranged on the visible-image capturing image sensor substrate 132-1. Then, the setting unit 21 can determine whether or not the visible-light signal intensity of any monitored pixel 1320 exceeds the setting signal intensity or whether or not the visible-light signal intensity of any monitored pixel 1320 is greater than the setting signal intensity, for each visible-light wavelength band. Thereby, the setting unit 21 can more appropriately control a light emission intensity of white light (visible light) from the white light source 221.

Figure 8:
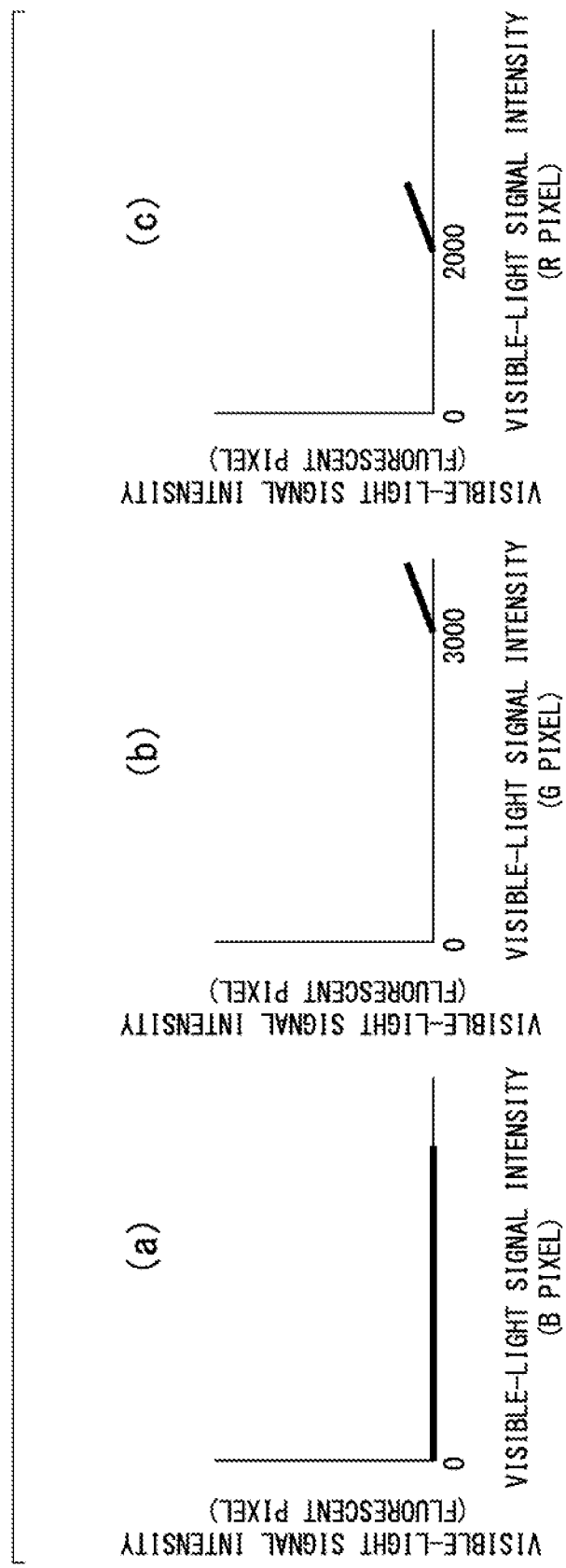
FIG. 8 is a diagram showing a method of setting an intensity of light emitted from a light source device provided in the fluorescence observation endoscope device according to the embodiment of the present invention.

FIG. 8 is a diagram showing a method of setting the intensity of light (illumination light, particularly visible light) emitted from the light source device 20 provided in the fluorescence observation endoscope device 1 according to the embodiment of the present invention. In (a) of FIG. 8 to (c) of FIG. 8, the horizontal axis represents a visible-light signal intensity detected by the visible-image capturing image sensor substrate 132-1, the vertical axis represents a visible-light signal intensity detected by the fluorescence-image capturing image sensor substrate 132-2, and a relationship between the visible-light signal intensity detected by the visible-image capturing image sensor substrate 132-1 and the visible-light signal intensity detected by the fluorescence-image capturing image sensor substrate 132-2 is shown. More specifically, in (a) of FIG. 8, a relationship between the visible-light signal intensity of the B pixel 1320B and the visible-light signal intensity of the fluorescent pixel 1320IR corresponding to the B pixel 1320B is shown. In (b) of FIG. 8, a relationship between the visible-light signal intensity of the G pixel 1320G and the visible-light signal intensity of the fluorescent pixel 1320IR corresponding to the G pixel 1320G is shown. In (c) of FIG. 8, a relationship between the visible-light signal intensity of the R pixel 1320R and the visible-light signal intensity of the fluorescent pixel 1320IR corresponding to the R pixel 1320R is shown. Also, in the following description, an example in which values of the visible-light signal intensity detected by the visible-image capturing image sensor substrate 132-1 and the visible-light signal intensity detected by the fluorescence-image capturing image sensor substrate 132-2, i.e., digital values representing magnitude of the pixel signals output by the pixels 1320, are represented as integers without units will be described.

As described above, the setting unit 21 gradually increases the light emission intensity of the white light (visible light) emitted from the white light source 221, for example, from a low level to a high level. At this time, the setting unit 21 monitors the visible-light signal intensity of each fluorescent pixel 1320IR arranged on the fluorescence-image capturing image sensor substrate 132-2 included in the parallel RAW data of the fluorescence-image capturing signal. When any visible-light signal intensity indicates a value, i.e., when any fluorescent pixel 1320IR allows exposure with (detects) visible light incident through the visible-image capturing image sensor substrate 132-1 and the dielectric multilayer film filter 13203, the setting unit 21 holds (records) the visible-light signal intensity of the pixel 1320 of the visible-image capturing image sensor substrate 132-1 corresponding to the fluorescent pixel 1320IR. Also, the setting unit 21 is configured to set a time when the value of any fluorescence signal intensity is changed by a predetermined value or more as a time when the fluorescent pixel 1320IR allows exposure with (detects) the visible light and the visible-light signal intensity of the corresponding pixel 1320 may be held (recorded). The setting unit 21 iterates the monitoring of the fluorescence signal intensity of the fluorescent pixel 1320IR and the holding (recording) of the visible-light signal intensity of the corresponding pixel 1320, and holds (records) a minimum visible-light signal intensity at a level of the light emission intensity of the current white light (visible light) for each pixel 1320 arranged on the visible-image capturing image sensor substrate 132-1, i.e., for each of the R pixel 1320R, the G pixel 1320G, and the B pixel 1320B. Then, the setting unit 21 is configured to set an allowed maximum visible-light signal intensity (digital value) or fixed visible-light signal intensity (digital value) as the setting signal intensity for each of the R pixel 1320R, the G pixel 1320G, and the B pixel 1320B on the basis of the relationship between the held (recorded) minimum visible-light signal intensity and the fluorescence signal intensity.

An example of the setting signal intensity to be set when the setting unit 21 holds the relationship between the visible-light signal intensity and the fluorescence signal intensity for each pixel 1320 as shown in (a) of FIG. 8 to (c) of FIG. 8 will be described.

As shown in (a) of FIG. 8, when the visible-light signal intensity of the fluorescent pixel 1320IR corresponding to the B pixel 1320B is "0" throughout the entire region of the visible-light signal intensity of the B pixel 1320B, the setting unit 21 does not set the setting signal intensity corresponding to the B pixel 1320B. That is, even if the light emission intensity of the white light source 221 is increased, the setting unit 21 does not set the setting signal intensity corresponding to the B pixel 1320B when the fluorescent pixel 1320IR corresponding to the B pixel 1320B has not allowed exposure with (detected) the visible light. Then, the setting unit 21 excludes the visible-light signal intensity of the B pixel 1320B from the object to be monitored.

Also, as shown in (b) of FIG. 8, if the visible-light signal intensity of the fluorescent pixel 1320IR corresponding to the G pixel 1320G indicates a value from when the visible-light signal intensity of the G pixel 1320G is "3000", the setting unit 21 sets the setting signal intensity corresponding to the G pixel 1320G. That is, when the light emission intensity of the white light source 221 is increased until the digital value representing the magnitude of the pixel signal output by the G pixel 1320G becomes "3000", the setting unit 21 determines that the fluorescent pixel 1320IR corresponding to the G pixel 1320G is detecting the visible light transmitted through the visible-image capturing image sensor substrate 132-1 and the dielectric multilayer film filter 13203 and the exposure (detection) accuracy of fluorescence of the wavelength band WD in the photoelectric conversion element 132021 has deteriorated. Thus, the setting unit 21 sets a value less than "3000" (for example, "2800") as the setting signal intensity corresponding to the G pixel 1320G by designating the visible-light signal intensity of the G pixel 1320G="3000" as a reference.

Also, as shown in (c) of FIG. 8, if the visible-light signal intensity of the fluorescent pixel 1320IR corresponding to the R pixel 1320R indicates a value from when the visible-light signal intensity of the R pixel 1320R is "2000", the setting unit 21 similarly sets the setting signal intensity corresponding to the R pixel 1320R. That is, when the light emission intensity of the white light source 221 is increased until the digital value representing the magnitude of the pixel signal output by the R pixel 1320R becomes "2000", the setting unit 21 determines that the fluorescent pixel 1320IR corresponding to the R pixel 1320R detects the visible light transmitted through the visible-image capturing image sensor substrate 132-1 and the dielectric multilayer film filter 13203 and the exposure (detection) accuracy of fluorescence of the wavelength band WD in the photoelectric conversion element 132021 deteriorates. Thus, the setting unit 21 sets a value less than "2000" (for example, "1800") as the setting signal intensity corresponding to the R pixel 1320R by designating the visible-light signal intensity of the R pixel 1320R="2000" as a reference.

In this manner, the setting unit 21 sets a setting signal intensity for each pixel 1320 arranged on the visible-image capturing image sensor substrate 132-1 on the basis of the visible-light signal intensity indicated by the parallel RAW data of the visible-image capturing signal and the fluorescence signal intensity indicated by the parallel RAW data of the fluorescence-image capturing signal included in each monitoring signal output from the image processing unit 32. Then, as described above, in the normal operation (the operation of observing the object 901) in the fluorescence observation endoscope device 1, the setting unit 21 monitors the visible-light signal intensity of each pixel 1320 and controls the light emission intensity of white light (visible light) from the white light source 221 in accordance with a determination result based on the setting signal intensity which has been set.

More specifically, for example, if the monitored visible-light signal intensity of the R pixel 1320R exceeds "1800" or becomes greater than "1800", the setting unit 21 controls the white light source 221 so that the light emission intensity is decreased. Also, for example, when the visible-light signal intensity of the monitored R pixel 1320R is a value of "1800" or less or a value in the vicinity of "1800" (e.g., "1800" to "1600"), the setting unit 21 controls the white light source 221 so that the current light emission intensity is maintained. Also, for example, when the monitored visible-light signal intensity of the R pixel 1320R becomes a value sufficiently less than "1800" (for example, "1500" or less), the setting unit 21 controls the white light source 221 so that the light emission intensity is increased. Also, in the present invention, the amount of control of the light emission intensity of the white light source 221 in the setting unit 21 is not particularly limited.

Thereby, in the fluorescence observation endoscope device 1, in the normal operation (the operation of observing the object 901), there is no incidence of visible light that has not been attenuated by the visible-image capturing image sensor substrate 132-1 and the dielectric multilayer film filter 13203 for the fluorescence-image capturing image sensor substrate 132-2 constituting the laminated image sensor 132. Thereby, the fluorescence observation endoscope device 1 can prevent the deterioration of the exposure (detection) accuracy of fluorescence in the photoelectric conversion elements of all the fluorescent pixels 1320IR arranged in the fluorescence-image capturing image sensor substrate 132-2. Thereby, the fluorescence observation endoscope device 1 can minimize the deterioration of image quality in the fluorescence image of the object 901 based on the fluorescence-image capturing signal obtained through exposure in the fluorescence-image capturing image sensor.

Also, the fluorescence observation endoscope device 1 can increase a light emission intensity of the white light (visible light) from the white light source 221 until it is determined that the exposure (detection) accuracy of fluorescence of the wavelength band WD in the photoelectric conversion element 132021 deteriorates. Thereby, the fluorescence observation endoscope device 1 does not unnecessarily darken the white light (visible light) emitted by the white light source 221 and can minimize the deterioration of image quality in the visible image of the object 901 based on a visible-image capturing signal obtained through exposure in the visible-image capturing image sensor.

Also, if the setting unit 21 sets the setting signal intensity without distinguishing a wavelength band of light (visible light), i.e., a color of the on-chip color filter 13204 corresponding to each pixel 1320, a smallest value within the visible-light signal intensities of the R pixel 1320R, the G pixel 1320G, and the B pixel 1320B when a value of the visible-light signal intensity of the fluorescent pixel 1320IR is indicated is set as a common setting signal intensity of the pixels 1320. More specifically, when the relationship between the visible-light signal intensity and the fluorescence signal intensity in each pixel 1320 is the relationship shown in (a) of FIG. 8 to (c) of FIG. 8, the setting unit 21 similarly sets a value less than "2000" (for example, "1800") as the setting signal intensity corresponding to all the pixels 1320 by designating the lowest visible-light signal intensity of the R pixel 1320R="2000" shown in (c) of FIG. 8 as a reference. Also, even when the setting unit 21 sets the setting signal intensity without distinguishing a color of the on-chip color filter 13204 corresponding to each pixel 1320, a method of controlling the light emission intensity of the white light source 221 to be performed by the setting unit 21 in the normal operation in the fluorescence observation endoscope device 1 is similar to that when the setting unit 21 sets the setting signal intensity while distinguishing a color of the on-chip color filter 13204 corresponding to each pixel 1320.

However, as described above, when the setting unit 21 sets the setting signal intensity while distinguishing a color of the on-chip color filter 13204 corresponding to each pixel 1320, it is possible to more appropriately control the light emission intensity of white light (visible light) from the white light source 221. More specifically, a case in which the relationship between the visible-light signal intensity and the fluorescence signal intensity in each pixel 1320 is the relationship shown in (a) of FIG. 8 to (c) of FIG. 8 is considered. When the setting unit 21 does not distinguish the pixels 1320, the setting signal intensity is set to "1800" as described above. Thus, when the visible-light signal intensity of the G pixel 1320G is, for example, "2500", the setting unit 21 controls the white light source 221 so that the light emission intensity is decreased. On the other hand, when the setting unit 21 distinguishes the pixels 1320, the setting signal intensity of the G pixel 1320G is set to "2800" as described above. Accordingly, even if the visible-light signal intensity of the G pixel 1320G is, for example, "2500", the setting unit 21 does not control the white light source 221 so that the light emission intensity is decreased, i.e., the setting unit 21 controls the white light source 221 so that the current light emission intensity is maintained. If the setting unit 21 does not distinguish the pixels 1320, control is performed so that the light emission intensity of the white light source 221 is decreased despite the fact that the exposure (detection) accuracy of fluorescence of the wavelength band WD in the photoelectric conversion element 132021 of the corresponding fluorescent pixel 1320IR does not deteriorate unless the visible-light signal intensity of the G pixel 1320G becomes "3000" or more. This indicates that, if the setting unit 21 does not distinguish the pixels 1320, control may be performed so that the light emission intensity of the white light source 221 is decreased early, i.e., with a margin, even when the visible-light signal intensity of the pixel 1320 is less than the visible-light signal intensity in which the exposure (detection) accuracy of fluorescence of the wavelength band WD in the photoelectric conversion element 132021 of the corresponding fluorescent pixel 1320IR deteriorates. However, if the setting unit 21 does not distinguish the pixels 1320, there is also an advantage in that a process of monitoring the visible-light signal intensity of each pixel 1320 is easily performed in the normal operation in the fluorescence observation endoscope device 1 as described above.

Also, the setting unit 21 may be configured to notify the image processing unit 32 provided in the external processing unit 30 of information indicating that the light emission intensity of the white light source 221 has been controlled. In this case, when image processing is performed on the parallel RAW data output from the deserializer 31, the image processing unit 32 can generate a visible image (from which the object 901 is more easily viewed) or display an image (display image data) with high image quality by changing a method or parameters of image processing (for example, a gamma correction process) in accordance with a notification from the setting unit 21.

Also, in the present invention, a timing at which the setting unit 21 performs a process of setting the setting signal intensity is not particularly limited. However, in the laminated image sensor 132, a relationship between the pixels 1320 (the R pixel 1320R, the G pixel 1320G, and the B pixel 1320B) arranged on the visible-image capturing image sensor substrate 132-1, the dielectric multilayer film filter 13203, and the corresponding pixels 1320 (fluorescent pixels 1320IR) arranged on the fluorescence-image capturing image sensor substrate 132-2 is basically constant. This is because, after the fluorescence observation endoscope device 1 is assembled, the structure of the laminated image sensor 132 does not change, i.e., the visible-image capturing image sensor substrate 132-1, the dielectric multilayer film filter 13203, and the fluorescence-image capturing image sensor substrate 132-2 are not changed (replaced) in the structure of the laminated image sensor 132, as a matter of principle. Accordingly, in the laminated image sensor 132, a constant relationship between the visible-light signal intensity in each of the R pixel 1320R, the G pixel 1320G, and the B pixel 1320B and the fluorescence signal intensity in the corresponding fluorescent pixel 1320IR is fixed. Thus, for example, the setting unit 21 may set the setting signal intensity by performing a process of setting a setting signal intensity at least once before the fluorescence observation endoscope device 1 is assembled and shipped. That is, the setting unit 21 may not re-perform the process of setting the setting signal intensity.

In this manner, the setting unit 21 provided in the light source device 20 constituting the fluorescence observation endoscope device 1 controls a light emission intensity of the white light emitted from the white light source 221 on the basis of the monitoring signal input from the external processing unit 30. Thereby, the light source device 20 can prevent the deterioration of the exposure (detection) accuracy of fluorescence and minimize the deterioration of image quality of the visible image when the laminated image sensor 132 simultaneously performs the normal photographing of the object 901 with visible light and the fluorescence photographing of the object 901 with fluorescence emitted by exciting ICG administrated according to radiation of excitation light such as near-infrared light.

According to an embodiment, there is provided a fluorescence observation device (the fluorescence observation endoscope device 1), including: a light source device (the light source device 20) configured to irradiate an object with light including wavelength bands of visible light and excitation light (near-infrared light); an imaging device (the laminated image sensor 132) including a first substrate (the visible-image capturing image sensor substrate 132-1) on which a plurality of first photoelectric conversion elements (the photoelectric conversion elements 132011 constituting the R pixels 1320R, the G pixels 1320G, and the B pixels 1320B) are formed, a second substrate (the fluorescence-image capturing image sensor substrate 132-2) on which a plurality of second photoelectric conversion elements (the photoelectric conversion elements 132021 constituting the fluorescent pixels 1320IR) are formed, and an interlayer filter (the dielectric multilayer film filter 13203) arranged between the visible-image capturing image sensor substrate 132-1 and the fluorescence-image capturing image sensor substrate 132-2, the photoelectric conversion elements 132011 being configured to detect light of a visible region within reflected light reflected from the object, the photoelectric conversion elements 132021 being configured to detect light of an infrared region (fluorescence) within the reflected light transmitted through the visible-image capturing image sensor substrate 132-1, and the dielectric multilayer film filter 13203 being configured to attenuate the light of the visible region transmitted through the visible-image capturing image sensor substrate 132-1 (the reflected light (the visible light)); and a setting device (the setting unit 21) configured to set a light emission intensity of the visible light radiated by the light source device 20 (white light emitted by the white light source 221, i.e., visible light separated by the dichroic mirror 231) so that each photoelectric conversion element 132011 is able to detect the visible light and a detection value of light detected by each photoelectric conversion element 132021 become less than or equal to a predetermined value (an appropriate level at which the exposure (detection) accuracy of fluorescence is not deteriorated).

Also, according to the embodiment, the fluorescence observation device (the fluorescence observation endoscope device 1) is configured in which the light source device 20 is configured to independently set the light emission intensity of the visible light (white light emitted by the white light source 221) and a light emission intensity of the excitation light (the near-infrared light) and the setting unit 21 is configured to set the light emission intensity of the visible light (the white light emitted by the white light source 221) irradiated by the light source device 20 on the basis of a first detection intensity (a visible-light signal intensity) which is an intensity of light of the visible region (reflected light (visible light)) included in the reflected light detected by each photoelectric conversion element 132011.

Also, according to the embodiment, the fluorescence observation device (the fluorescence observation endoscope device 1) is configured in which, when the visible-light signal intensity detected by one of the photoelectric conversion element exceeds a preset maximum detection intensity, the setting unit 21 is configured to set the light emission intensity of the visible light (the white light emitted by the white light source 221) so that the visible-light signal intensity detected by each photoelectric conversion element 132011 becomes less than or equal to the maximum detection intensity (setting signal intensity).

Also, according to the embodiment, the fluorescence observation device (the fluorescence observation endoscope device 1) is configured in which the setting unit 21 is configured to set the light emission intensity of the visible light (the white light emitted by the white light source 221) at a timing synchronized with a cycle in which each photoelectric conversion element 132011 detects the visible-light signal intensity (a frame rate).

Also, according to the embodiment, the fluorescence observation device (the fluorescence observation endoscope device 1) is configured in which the setting unit 21 is configured to monitor a second detection intensity (a fluorescence signal intensity) while gradually changing the light emission intensity of the visible light (the white light emitted by the white light source 221) (for example, while gradually increasing the light emission intensity from a low level to a high level at a preset light emission intensity level intensity), the setting unit 21 is configured to store (hold) a level of the visible-light signal intensity detected by the corresponding photoelectric conversion element 132011 when a level of the fluorescence signal intensity has been changed by an amount greater than or equal to a predetermined value (for example, when the photoelectric conversion element 132021 has allowed (exposure with) (detected) the visible light), and the fluorescence signal intensity is an intensity of light detected by each photoelectric conversion element 132021, the setting unit 21 is configured to set the maximum detection intensity (setting signal intensity) on the basis of the stored (held) level of the visible-light signal intensity.

Also, according to the embodiment, the fluorescence observation device (the fluorescence observation endoscope device 1) is configured in which the photoelectric conversion element 132011 corresponds to light of a visible region of any one of a visible region of a first wavelength band, a second wavelength band, and a third wavelength band, the first wavelength band is wavelength band from light of a visible region (for example, light of a wavelength band of 400 nm to 500 nm), the second wavelength band is wavelength band of a visible region and different from the first wavelength band (for example, light of a wavelength band of 500 nm to 600 nm), the third wavelength band is wavelength band of a visible region and different from both of the first wavelength band and the second wavelength band (for example, light of a wavelength band of 600 nm to 700 nm), the setting unit 21 is configured to store (hold) a minimum level of the visible-light signal intensity for each of the wavelength band corresponding to the photoelectric conversion element 132011, and the setting unit 21 is configured to set the maximum detection intensity (setting signal intensity) corresponding to each of the visible region of the first wavelength band, the visible region of the second wavelength band, and the visible region of the third wavelength band on the basis of each stored (held) minimum level of the visible-light signal intensity.

Also, according to the embodiment, the fluorescence observation device (the fluorescence observation endoscope device 1) is configured in which the setting unit 21 is configured to set the light emission intensity of the visible light (the white light emitted by the white light source 221) so that the detection intensity becomes a preset intensity (setting signal intensity).

Also, according to the embodiment, the fluorescence observation device (the fluorescence observation endoscope device 1) is configured in which the setting unit 21 is configured to set the light emission intensity of the visible light (the white light emitted by the white light source 221) at a timing synchronized with a cycle in which each photoelectric conversion element 132011 detects the visible-light signal intensity (a frame rate).

Also, according to the embodiment, the fluorescence observation device (the fluorescence observation endoscope device 1) is configured in which the setting unit 21 is configured to monitor a fluorescence signal intensity while gradually changing the light emission intensity of the visible light (the white light emitted by the white light source 221) (for example, gradually increasing the light emission intensity from a low level to a high level at an interval of a predetermined emission intensity level), the setting unit 21 is confirmed to store (hold) a level of the visible-light signal intensity detected by the corresponding photoelectric conversion element 132011 when a level of the fluorescence signal intensity has been changed by an amount greater than or equal to a predetermined value (for example, the photoelectric conversion element 132021 has allowed exposure with (detected) the visible light), and the fluorescence signal intensity is an intensity of light detected by each photoelectric conversion element 132021, the setting unit 21 is configured to set the fixed detection intensity (setting signal intensity) on the basis of the stored (held) level of the visible-light signal intensity.

Also, according to the embodiment, the fluorescence observation device (the fluorescence observation endoscope device 1) is configured in which the photoelectric conversion element 132011 corresponds to light of a visible region of any one a visible region of a first wavelength band, a second wavelength band, and l a third wavelength band, the first wavelength band is wavelength band from light of a visible region (for example, light of a wavelength band of 400 nm to 500 nm), the second wavelength band is wavelength band of a visible region and different from the first wavelength band (for example, light of a wavelength band of 500 nm to 600 nm), the third wavelength band is wavelength band of a visible region and different from both of the first wavelength band and the second wavelength band (for example, light of a wavelength band of 600 nm to 700 nm), the setting unit 21 is configured to store (hold) a minimum level of the visible-light signal intensity for each of the wavelength band corresponding to the photoelectric conversion element 132011, and the setting unit 21 is configured to set the fixed detection intensity (setting signal intensity) corresponding to each of the visible region of the first wavelength band, the visible region of the second wavelength band, and the visible region of the third wavelength band on the basis of each stored (held) minimum level of the visible-light signal intensity.

Also, according to the embodiment, the fluorescence observation device (the fluorescence observation endoscope device 1) is configured in which the dielectric multilayer film filter 13203 is a dielectric multilayer film filter.

Also, according to the embodiment, there is provided a fluorescence observation endoscope device (the fluorescence observation endoscope device 1) for observing a fluorescent material (for example, a fluorescent material including derivative-labeled antibody indocyanine green (ICG)), including: a fluorescence observation device which includes the light source device 20 configured to irradiate an object to be examined with light including wavelength bands of visible light and excitation light (near-infrared light) for causing the object to be examined to emit fluorescence by irradiating the fluorescent material with light, the laminated image sensor 132 including the visible-image capturing image sensor substrate 132-1 on which a plurality of photoelectric conversion elements are formed, the fluorescence-image capturing image sensor substrate 132-2 on which a plurality of photoelectric conversion elements 132021 are formed, and the dielectric multilayer film filter 13203 arranged between the visible-image capturing image sensor substrate 132-1 and the fluorescence-image capturing image sensor substrate 132-2; the photoelectric conversion elements 132011 being configured to detect light of a visible region within reflected light reflected from the object to be examined (the object 901), the photoelectric conversion elements 132021 being configured to detect the fluorescence within the reflected light transmitted through the visible-image capturing image sensor substrate 132-1, and the dielectric multilayer film filter 13203 being configured to attenuate the light of the visible region transmitted through the visible-image capturing image sensor substrate 132-1; and the setting unit 21 configured to set a light emission intensity of the visible light radiated by the light source device 20 (white light emitted by the white light source 221. i.e., visible light separated by the dichroic mirror 231) so that each photoelectric conversion element 132011 is able to detect the visible light and a detection value (exposure (detection) accuracy) of fluorescence detected by each photoelectric conversion element 132021 become less than or equal to a predetermined value (an appropriate level at which the exposure (detection) accuracy of the fluorescence is not deteriorated).

Also, according to the embodiment, the fluorescence observation endoscope device 1 is configured in which the laminated image sensor 132 is arranged at a distal end (the imaging unit 13 provided at the distal end of the insertion unit 11) of an insertion unit (the insertion unit 11) of the fluorescence observation endoscope device 1 to be inserted into a living body (a person to be examined to which the fluorescence material including ICG is administrated).

As described above, according to the embodiment of the present invention, a solid-state imaging device provided in a fluorescence observation device includes a visible-image capturing image sensor configured to allow exposure with (detect) light of a visible region (visible light), a fluorescence-image capturing image sensor configured to allow exposure with (detect) light of an infrared region (near-infrared light), and an interlayer filter arranged between the visible-image capturing image sensor and the fluorescence-image capturing image sensor. According to the embodiment of the present invention, in the light source device provided in the fluorescence observation device, white light of the wavelength band of visible light and white light of the wavelength band of excitation light are radiated as illumination light to the object to be examined. Thereby, according to the embodiment of the present invention, the fluorescence observation device can obtain a visible-image capturing signal obtained by allowing exposure with visible light and a fluorescence-image capturing signal obtained by allowing exposure with fluorescence which is light of an infrared region (near-infrared light) emitted through excitation of a derivative-labeled antibody (fluorescent agent: fluorescent material) such as ICG administered to the object to be examined in the same period.

Also, according to the embodiment of the present invention, the light source device provided in the fluorescence observation device monitors the visible-light signal intensity indicated by the visible-image capturing signal. In the embodiment of the present invention, the light source device provided in the fluorescence observation device determines the monitored visible-light signal intensity on the basis of a preset setting signal intensity and controls a light emission intensity of white light of an emitted visible-light wavelength band in accordance with a determination result. Thereby, according to the embodiment of the present invention, the solid-state imaging device provided in the fluorescence observation device can prevent visible light which has not been attenuated by the visible-image capturing image sensor and the interlayer filter from being incident on the fluorescence-image capturing image sensor. Thereby, according to the embodiment of the present invention, the fluorescence observation device can prevent the deterioration of exposure (detection) in the fluorescence-image capturing image sensor provided in the solid-state imaging device due to unnecessarily increasing the light emission intensity of white light of a wavelength band of visible light emitted by the light source device. Thereby, according to the embodiment of the present invention, the fluorescence observation device can minimize the deterioration of image quality in a fluorescence image of an object to be examined based on a fluorescence-image capturing signal obtained through exposure in the fluorescence-image capturing image sensor provided in the solid-state imaging device.

Also, according to the embodiment of the present invention, the light source device provided in the fluorescence observation device can increase a light emission intensity of white light of an emitted visible-light wavelength band immediately before it is determined that the exposure (detection) accuracy of fluorescence in the fluorescence-image capturing image sensor provided in the solid-state imaging device has deteriorated. Thereby, according to the embodiment of the present invention, the fluorescence observation device can minimize the deterioration of image quality of a visible image of an object to be examined based on a visible-image capturing signal obtained through exposure in the visible-image capturing image sensor provided in the solid-state imaging device without unnecessarily decreasing the light emission intensity of white light of a wavelength band of visible light emitted by the light source device.

Thereby, according to the embodiment of the present invention, the fluorescence observation device can include a solid-state imaging device in which the visible-image capturing image sensor and the fluorescence-image capturing image sensor are laminated and obtain a visible image of an object to be examined and a fluorescence image of an object to be examined in the same period in a state in which the deterioration of image quality is minimized. Thereby, according to the embodiment of the present invention, even when the fluorescence observation device is configured as a fluorescence observation endoscope device, it is possible to present a visible image of an object to be examined and a fluorescence image of an object to be examined to an examiner in the same period in a state in which the deterioration of image quality is minimized.

Also, in the embodiment of the present invention, a case in which an imaging signal output by the solid-state imaging device provided in the imaging unit constituting the fluorescence observation device of the present invention (the visible-image capturing image sensor and the fluorescence-image capturing image sensor constituting the laminated image sensor 132 in the embodiment) is a pixel signal according to signal charges obtained through photoelectric conversion performed in each pixel in the pixel unit, i.e., RAW data has been described. However, a type of imaging signal output by the solid-state imaging device is not limited to the RAW data described in the embodiment of the present invention. For example, in order to reduce the amount of data of the imaging signal transmitted by the laminated image sensor 132 through the imaging signal line 61, for example, a pixel signal of each of the R pixel 1320R, the G pixel 1320G, and the B pixel 1320B may be converted into a so-called luminance color difference signal such as a YCbCr signal or a YUV signal by performing a YC process on the pixel signal and the luminance color difference signal may be output. In this case, a configuration in which the serializer 1324 externally outputs a serial luminance color difference signal obtained through parallel/serial conversion as a visible-image capturing signal after a pixel signal of a digital value output by the analog/digital conversion unit 1323 is converted into a luminance color difference signal of a digital value is conceived for the visible-image image sensor. Also, in this case, a configuration in which the external processing unit 30 generates image data including a pixel signal of any pixel of the R pixel, the G pixel, and the B pixel according to a demosaicing process of the image processing unit 32 after the deserializer 31 restores the serial luminance color difference signal to the original parallel luminance color difference signal is conceived.

Also, in the embodiment of the present invention, a configuration in which the light source device constituting the fluorescence observation device of the present invention emits light of a predetermined wavelength band according to a set of a white light source and a dichroic mirror is shown. However, the configuration of the light source device is not limited to the configuration shown in the embodiment of the present invention. For example, instead of the set of the white light source and the dichroic mirror, a configuration in which a light source configured to emit light of a predetermined wavelength band is provided and a light irradiation lens concentrates light emitted from each light source and emits the concentrated light may be adopted. In this case, for example, the light source device may be configured to include each of a white light source configured to emit light of a wavelength band from blue (B) to red (R) (for example, visible light of a wavelength band of 400 nm to 700 nm) and an infrared light source configured to emit light of an excitation-light wavelength band (for example, near-infrared light of a wavelength band of 700 nm to 800 nm).

Also, according to the embodiment of the present invention, a case in which the fluorescence observation device of the present invention is configured as a fluorescence observation endoscope device has been described. However, the fluorescence observation device of the present invention is not limited to a configuration serving as the fluorescence observation endoscope device shown in the embodiment. For example, the fluorescence observation device of the present invention can be configured as a microscope device. In this case, the components of the fluorescence observation device of the present invention are arranged at appropriate positions in the microscope device.

Also, for example, the number of thin-film layers of each of silicon dioxide ($SiO_2$) and titanium oxide ($TiO_2$) may be reduced if it is possible to maintain allowable image quality for a visible image with an attenuation rate (a light shielding rate) for visible light of a wavelength band of 450 nm or 450 nm or less to 750 nm when a light emission intensity of white light (visible light) from the white light source 221 is weakened with respect to characteristics of the dielectric multilayer film filter 13203 laminated on the laminated image sensor 132. Finally, a configuration in which the dielectric multilayer film filter layer 132-3 is not laminated on the laminated image sensor 132 may be adopted. In the laminated image sensor 132 of this configuration, it is possible to further minimize the deterioration of a sensitivity and oblique incidence characteristics for light in the photoelectric conversion element 132021 of each fluorescent pixel 1320IR arranged on the fluorescence-image capturing image sensor substrate 132-2.

While preferred embodiments of the present invention have been described and shown above, the present invention is not limited to the embodiments and modified examples thereof. Within a range not departing from the gist or spirit of the present invention, additions, omissions, substitutions, and other modifications to the configuration can be made.

Also, the present invention is not to be considered as being limited by the foregoing description, and is limited only by the scope of the appended claims.

What is claimed is:

1. A fluorescence observation device, comprising:
    a light source device configured to irradiate an object with light including wavelength bands of visible light and excitation light;
    an imaging device including a first substrate on which a plurality of first photoelectric conversion elements are formed and which has a first wiring layer provided on a side of the first substrate opposite to a side on which light is incident on the first photoelectric conversion elements, a second substrate on which a plurality of second photoelectric conversion elements are formed and which has a second wiring layer provided on a side of the second substrate opposite to a side on which light is incident on the second photoelectric conversion elements, and an interlayer filter arranged between the first substrate and the second substrate, the a first photoelectric conversion element of the plurality of first photoelectric conversion elements being configured to detect light of a visible region within reflected light reflected from the object, the a second photoelectric conversion element of the plurality of second photoelectric conversion elements being configured to detect light of an infrared region within the reflected light transmitted through the first substrate, and the interlayer filter being configured to attenuate the light of the visible region transmitted through the first substrate; and
    a setting controller configured to set a light emission intensity of the visible light radiated by the light source device so that each first photoelectric conversion element elements is able to detect the visible light, and a detection value of light detected by each second photoelectric conversion element become less than or equal to a predetermined value,
    wherein the first wiring layer has an opening that guides light through the second substrate.

2. The fluorescence observation device according to claim 1,
    wherein the light source device is configured to independently set the light emission intensity of the visible light and a light emission intensity of the excitation light, and wherein the setting controller is configured to set the light emission intensity of the visible light irradiated by the light source device on the basis of a first detection intensity which is an intensity of light of the visible region included in the reflected light detected by each first photoelectric conversion element.

3. The fluorescence observation device according to claim 2, wherein, when the first detection intensity detected by one of the first photoelectric conversion elements exceeds a preset maximum detection intensity, the setting controller is configured to set the light emission intensity of the visible light so that the first detection intensity detected by each first photoelectric conversion element becomes less than or equal to the maximum detection intensity.

4. The fluorescence observation device according to claim 3, wherein the setting controller is configured to set the light emission intensity of the visible light at a timing synchronized with a cycle in which each first photoelectric conversion element detects the first detection intensity.

5. The fluorescence observation device according to claim 4, wherein the setting controller is configured to monitor a second detection intensity while gradually changing the light emission intensity of the visible light, wherein the setting controller is configured to store a level of the first detection intensity detected by the corresponding first photoelectric conversion element when a level of the second detection intensity has been changed by an amount greater than or equal to a predetermined value, and wherein the second detection intensity is an intensity of light detected by each second photoelectric conversion element, wherein the setting controller is configured to set the maximum detection intensity on the basis of the stored level of the first detection intensity.

6. The fluorescence observation device according to claim 5, wherein the first photoelectric conversion element corresponds to light of a visible region of any one of a visible region of a first wavelength band, a second wavelength band, and a third wavelength band, wherein the first wavelength band is wavelength band from light of a visible region, the second wavelength band is wavelength band of a visible region and different from the first wavelength band, the third wavelength band is wavelength band of a visible region and different from both of the first wavelength band and the second wavelength band, wherein the setting controller is configured to store a minimum level of the first detection intensity for each of the wavelength band corresponding to the first photoelectric conversion element, and wherein the setting controller is configured to set the maximum detection intensity corresponding to each of the visible region of the first wavelength band, the visible region of the second wavelength band, and the visible region of the third wavelength band on the basis of each stored minimum level of the first detection intensity.

7. The fluorescence observation device according to claim 2, wherein the setting controller is configured to set the light emission intensity of the visible light so that the first detection intensity becomes a preset intensity.

8. The fluorescence observation device according to claim 7, wherein the setting controller is configured to set the light emission intensity of the visible light at a timing synchronized with a cycle in which each first photoelectric conversion element detects the first detection intensity.

9. The fluorescence observation device according to claim 8, wherein the setting controller is configured to monitor a second detection intensity while gradually changing the light emission intensity of the visible light, wherein the setting controller is configured to store a level of the first detection intensity detected by the corresponding first photoelectric conversion element when a level of the second detection intensity has been changed by an amount greater than or equal to a predetermined value, and wherein the second detection intensity is an intensity of light detected by each second photoelectric conversion element, wherein the setting controller is configured to set the a fixed detection intensity on the basis of the stored level of the first detection intensity.

10. The fluorescence observation device according to claim 9, wherein the first photoelectric conversion element corresponds to light of a visible region of any one of a visible region of a first wavelength band, a second wavelength band, and a third wavelength band, wherein the first wavelength band is wavelength band from light of a visible region, the second wavelength band is wavelength band of a visible region and different from the first wavelength band, the third wavelength band is wavelength band of a visible region and different from both of the first wavelength band and the second wavelength band, wherein the setting controller is configured to store a minimum level of the first detection intensity for each of the wavelength band corresponding to the first photoelectric conversion element, and wherein the setting controller is configured to set the a fixed detection intensity corresponding to each of the visible region of the first wavelength band, the visible region of the second wavelength band, and the visible region of the third wavelength band on the basis of each stored minimum level of the first detection intensity.

11. The fluorescence observation device according to claim 1, wherein the interlayer filter is a dielectric multilayer film filter.

12. A fluorescence observation endoscope device for observing a fluorescent material, comprising:

a fluorescence observation device which includes a light source device configured to irradiate an object to be examined with light including wavelength bands of visible light and excitation light for causing the object to be examined to emit fluorescence by irradiating the fluorescent material with light, an imaging device including a first substrate on which a plurality of first photoelectric conversion elements are formed and which has a first wiring layer provided on a side of the first substrate opposite to a side on which light is incident on the first photoelectric conversion elements, a second substrate on which a plurality of second photoelectric conversion elements are formed and which has a second wiring layer provided on a side of the second substrate opposite to a side on which light is incident on the second photoelectric conversion elements, and an interlayer filter arranged between the first substrate and the second substrate, the a first photoelectric conversion element of the plurality of first photoelectric conversion elements being configured to detect light of a visible region within reflected light reflected from the object to be examined, the a second photoelectric conversion element of the plurality of second photoelectric conversion elements being configured to detect the fluorescence within the reflected light transmitted through the first substrate, and the interlayer filter being configured to attenuate the light of the visible region transmitted through the first substrate; and a setting controller configured to set a light emission intensity of the visible light radiated by the light source device so that each first photoelectric conversion element elements is able to detect the visible light, and a detection value of the fluorescence detected by each second photoelectric conversion element become less than or equal to a predetermined value, wherein the first wiring layer has an opening that guides light through the second substrate.

13. The fluorescence observation endoscope device according to claim 12, wherein the imaging device is arranged at a distal end of an insertion unit of the fluorescence observation endoscope device to be inserted into a living body.

* * * * *